United States Patent [19]

Palmquist et al.

[11] Patent Number: 5,179,419
[45] Date of Patent: Jan. 12, 1993

[54] METHODS OF DETECTING, CLASSIFYING AND QUANTIFYING DEFECTS IN OPTICAL FIBER END FACES

[75] Inventors: John M. Palmquist, Lilburn, Ga.; Arthur T. Schmidt, Emmaus, Pa.; Behzad Shahraray, Freehold, N.J.

[73] Assignee: AT&T Bell Laboratories, Murray Hill, N.J.

[21] Appl. No.: 796,204

[22] Filed: Nov. 22, 1991

[51] Int. Cl.⁵ ............................................. G01N 21/84
[52] U.S. Cl. .................................. 356/73.1; 356/237; 382/1; 382/8
[58] Field of Search ................... 356/73.1, 237; 382/1, 382/8

[56] References Cited

U.S. PATENT DOCUMENTS 4,721,357  1/1988  Kovalchick et al. .............. 385/53 X
4,787,698  11/1988 Lyons et al. ....................... 385/60 X
4,802,726  2/1989  Palmquist et al. .

OTHER PUBLICATIONS

John Kesterson & Mike Richardson, *Confocal Microscope Capability with Desktop Affordability*, Advanced Imaging, Oct. 1991, at 23–26.

Cliff Glier, *Automated Machine Vision Microscopy for the Biologist*, Advanced Imaging, Oct. 1991, pp. 18–22.

Behzad Shahraray, et al., *Defect Detection, Classification and Quantification in Optical Fiber Connectors*, IAPR Workshop on Machine Vision Applications, Nov. 1990, pp. 15–22.

*Primary Examiner*—Vincent P. McGraw
*Attorney, Agent, or Firm*—E. W. Somers

[57] ABSTRACT

Methods are provided to detect, classify and quantify defects such as chips, pits, scratches and cracks in a polished end surface (31) of optical fiber and specifically in an end face of an optical fiber terminated by a ferrule (34). Images of the end face are acquired at each of three focal positions which collectively include all the features of interest. Information from these images is combined into a single image which is processed further. Discrepancies between the images are used to discriminate between cracks and scratches. Morphological processing is used to segment the fiber from its ferrule and a Hough transform is used to estimate the center and radius of the optical fiber, which facilitates the isolation of the fiber. Chips and pits in the fiber end face are detected and quantified by thresholding and morphological processing of the isolated fiber. Edge detection is used to detect edge segments resulting from scratches and cracks. Then the line segments are classified into scratches and cracks. The detected segments are matched to provide scratches in a final image. Quantitative measures then are used to establish standards for the quality of the polished, terminated optical fibers.

15 Claims, 19 Drawing Sheets

2-D ACCUMULATOR

1-D ACCUMULATOR (X)

1-D ACCUMULATOR (Y)

METHODS OF DETECTING, CLASSIFYING AND QUANTIFYING DEFECTS IN OPTICAL FIBER END FACES

TECHNICAL FIELD

This invention relates to methods of detecting, classifying and quantifying defects in optical fiber end faces. More particularly, this invention relates to machine vision systems and methods for detecting, classifying and quantifying defects in polished end surfaces of terminated optical fiber such as in end surfaces of ferrules which terminate optical fibers.

BACKGROUND OF THE INVENTION

Connections between optical transmission paths may be made by terminating optical fibers with plugs and by holding two such plugs which terminate optical fibers to be connected in predetermined positions with respect to each other. One such connection arrangement is referred to as a biconic connector which is disclosed in U.S. Pat. No. 4,512,630 which was issued on Apr. 23, 1985 in the name of P. K. Runge. In it, each optical fiber is terminated in a plug or ferrule having a truncated conical shape. Two such plugs are disposed in a biconical sleeve with small diameter end portions of the plugs being adjacent to a center plane. Another optical fiber connector is AT&T's ST ® connector which comprises a cylindrically shaped ferrule or plug that terminates an optical fiber. The plug is disposed within a cap and is biased outwardly. Two such plugs may be inserted into a sleeve having a longitudinal slot therein with the end faces of the plugs being in contact with each other or spaced apart by an attenuator.

Typically an end portion of an optical fiber which is inserted into a passageway in a ferrule, for example, is held assembled to the ferrule by epoxy. The ferrule which terminates an optical fiber may be made of any of several materials. For example, connector ferrules have been made of ceramic, plastic or glass materials. After the epoxy has cured, the end face of the end portion of each optical fiber which is terminated by the ferrule needs to be polished to remove excess epoxy and provide a surface for light to enter or exit the fiber. After an optical fiber has been inserted into a passageway of the plug, an end portion of the fiber which extends beyond the end face of the plug is cleaved. This is a relatively rough, imprecise operation which leaves a portion of fiber extending beyond the end face of the plug.

In order to achieve low loss, low reflectance connections, the end faces of the two plugs in which the optical fibers terminate need to have surfaces which are substantially normal to the longitudinal axes of the plugs and which may have optical fibers protruding slightly therefrom and being smoothly polished. Otherwise, the surfaces may be skewed to each other and/or surface roughness may cause the end faces of the fiber cores not to be substantially in engagement with each other or in engagement with an attenuator that may be disposed between the end faces. The protruding end must be polished so that an end face of the fiber is coplanar with or protrudes slightly from the end face of the plug.

Polishing is performed in order to remove scratches. Otherwise, scratches which are too large can scatter light and cause reflections. They interfere with the mating of connectors and prevent the achieving of low loss. The presence of dirt, cracks, chips, scratches or pits in the core region of the optical fiber can cause increased insertion loss or lead to premature failure due to the propagation of cracks under variable environmental or mechanical stress. What is sought is a connector in which a minimum of light is reflected. Of course, every time there is an interface between two connectors, some reflections occur. The quality of the polishing operation is the key to achieving low reflections. In fact, some manufacturers grade their products by the quality of the polishing.

In the prior art, polishing of end faces of connector plugs and fiber has been accomplished manually. A connector plug to be polished is mounted in a fixture and the fixture is moved in oscillating circular patterns with the end face of the fiber and subsequently the plug in engagement with a polishing surface of a predetermined grit size. Such a fixture which may be used to polish an end face of a truncated conically shaped connector plug is disclosed in U.S. Pat. No. 4,539,779 which was issued on Sep. 10, 1985 in the name of F. R. Weaver. Such fixtures are still commonly used by craftspersons when making fiber terminations in the field.

The manual polishing of fiber and connector plug end faces is not without problems. It should be apparent that such a procedure is subject to operator variations in pressure applied to the fixture and hence that between grit of the polishing surface and the end faces. Also, the length of time, the motion and the path along which the plug traverses may vary from plug to plug thus producing inconsistent results in fiber end face protrusion and extent of polish. Variations in polishing media, as well as internal stresses in fibers and external contamination can contribute to variations in the polished surface.

Also available in the prior art is apparatus for gang-polishing a plurality of connector plugs. Each of a plurality of plugs to be polished is mounted in a nest of a clamping ring. Then the clamping ring is moved desirably to cause ends of fibers protruding from the plugs to engage a polishing surface. The problems with such an apparatus are twofold. One problem is that when the fibers are cleaved, the length of fiber that extends beyond an end face of the plug varies significantly from plug to plug. When a plurality, for example, eight or twelve, are gang-polished, the fibers extending from several of the plugs may be longer and hence experience greater pressure as forces are applied to the clamping ring for the plurality of plugs. This greatly increases the possibility of cracking those fibers which extend farther from associated plug end faces than others. Secondly, the plugs may vary in length and yet be within prescribed tolerance limits. As a result of the variations in plug length, some of the plugs may be under-polished whereas others may be over-polished.

Of course, other more sophisticated polishing techniques in which the entire face of the terminating ferrule is polished are available. However, the apparatus for carrying out such techniques is relatively expensive.

In the past, end faces of fiber terminating devices which have been prepared with the hereinbefore described apparatus have been inspected by human vision under microscopes. Such an inspection is not one hundred percent reliable inasmuch as it depends on the visual acuity of a human being as well as on the quality of the optical apparatus which is used for inspection. Further, such inspection is very subjective. A production worker can apply rules but is very difficult to quantify the number of scratches in an end surface of a fiber, for example. Very fine cracks can occur which are difficult for human inspectors to detect, even with the best optical aids such as high power microscopes. Cracks are a critical defect inasmuch as they can propagate under mechanical or environmental stress and lead to premature, catastrophic failure of the interconnection. The lack of consistent quantitative measures for detecting defects has been a major obstacle to the development of quality standards for connectors.

It is desirable to improve manufacturing processes to the point where defects in connectorized optical fibers become so rare that 100% inspection is not required. Experience to date shows that 100% inspection for the final polishing of optical fiber connectors is still required.

What is sought after and what does not appear to be available in the prior art are methods and apparatus which are capable of reliably and consistently detecting, measuring and classifying defects in end surfaces of optical fiber connector elements. What is needed and what is not provided in the prior art is an objective measurement method for classifying and quantifying defects so that changes and improvements in processes can be accurately measured. Such methods and apparatus should be capable of being used for optical fiber connector elements which are made of any of a variety of materials.

SUMMARY OF THE INVENTION

The foregoing problems of the prior art have been overcome with the methods of this invention. A method of detecting, classifying and quantifying defects in a polished end face of an optical fiber comprises the steps of acquiring images of an end face of a fiber at an optimum focal position and at auxiliary positions behind and in front of the optimum focal position. A combined image of the fiber end face which depicts any features of interest which exist only in the end face of the optical fiber is generated. Then features of interest which exist only in the end face of the optical fiber are identified. Quantitative data generated for each of the features of interest are compared with acceptable values to determine the acceptability of the polished end face of the optical fiber.

For an optical fiber end portion which has been terminated by a connector component with an end face of the fiber exposed at an end face of the component, a combined image of the terminated fiber end face depicts any features of interest which exist only in the fiber end face and in the end face of the connector component. The end face of the optical fiber is isolated from materials of the connector component to provide an image which depicts any features of interest which exist only in the end face of the optical fiber.

BRIEF DESCRIPTION OF THE DRAWING

Other features of the present invention will be more readily understood from the following detailed description of specific embodiments thereof when read in conjunction with the accompanying drawings, in which.

DETAILED DESCRIPTION

Figure 1:
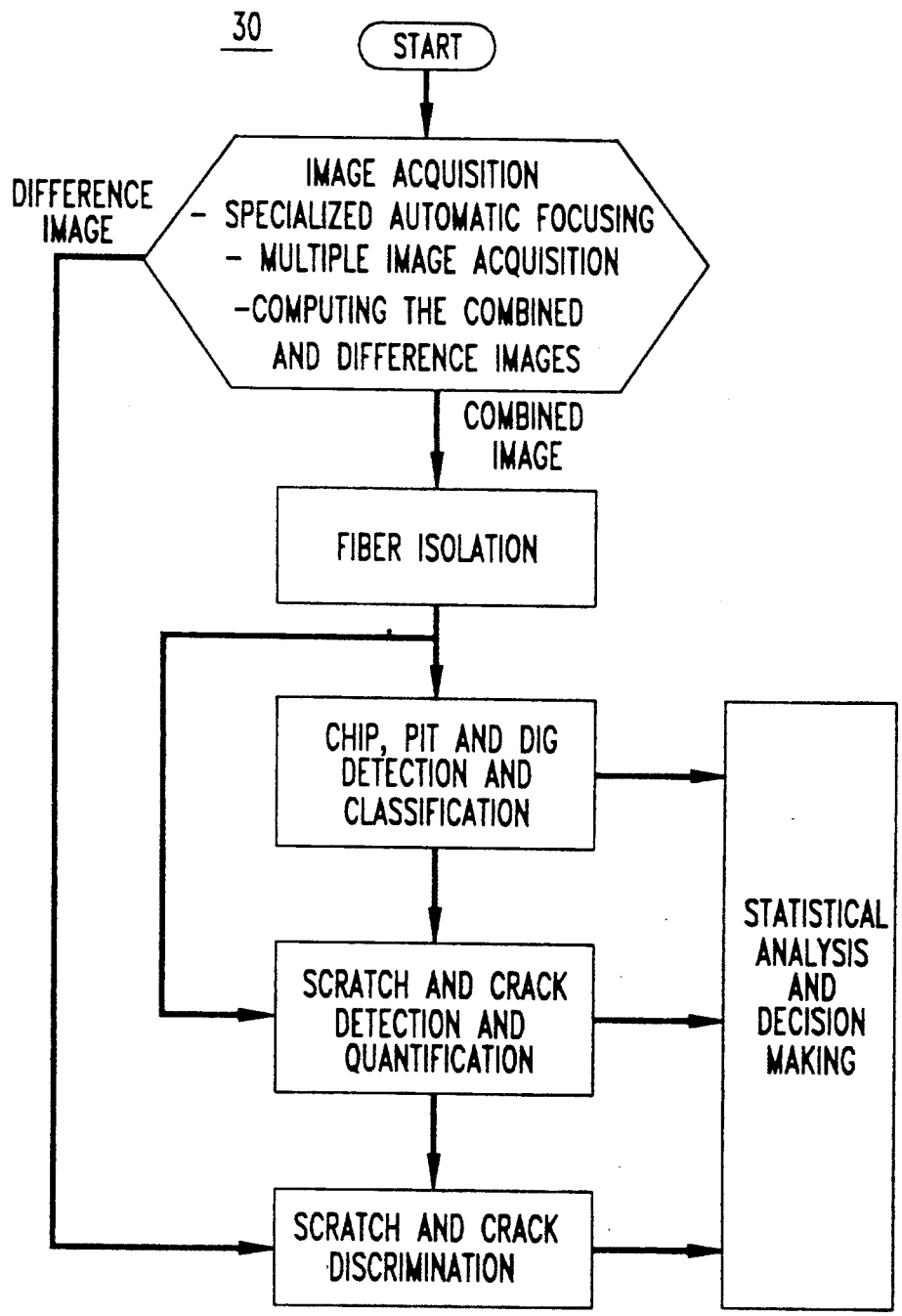
FIG. 1 is a flow chart which depicts a method of this invention for detecting and quantifying defects in an end face of a terminated optical fiber.
Figure 2:
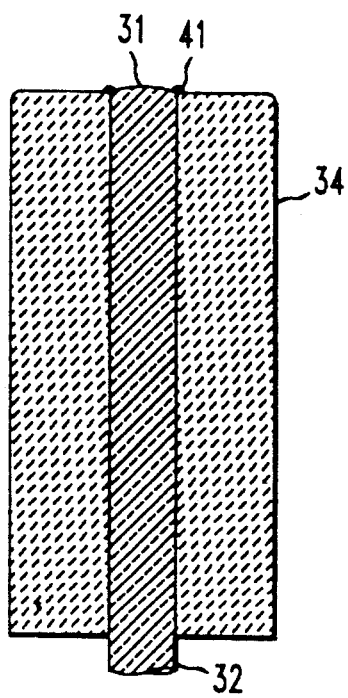
FIG. 2 is an enlarged longitudinal sectional view of a terminated end portion of optical fiber.
Figure 3:
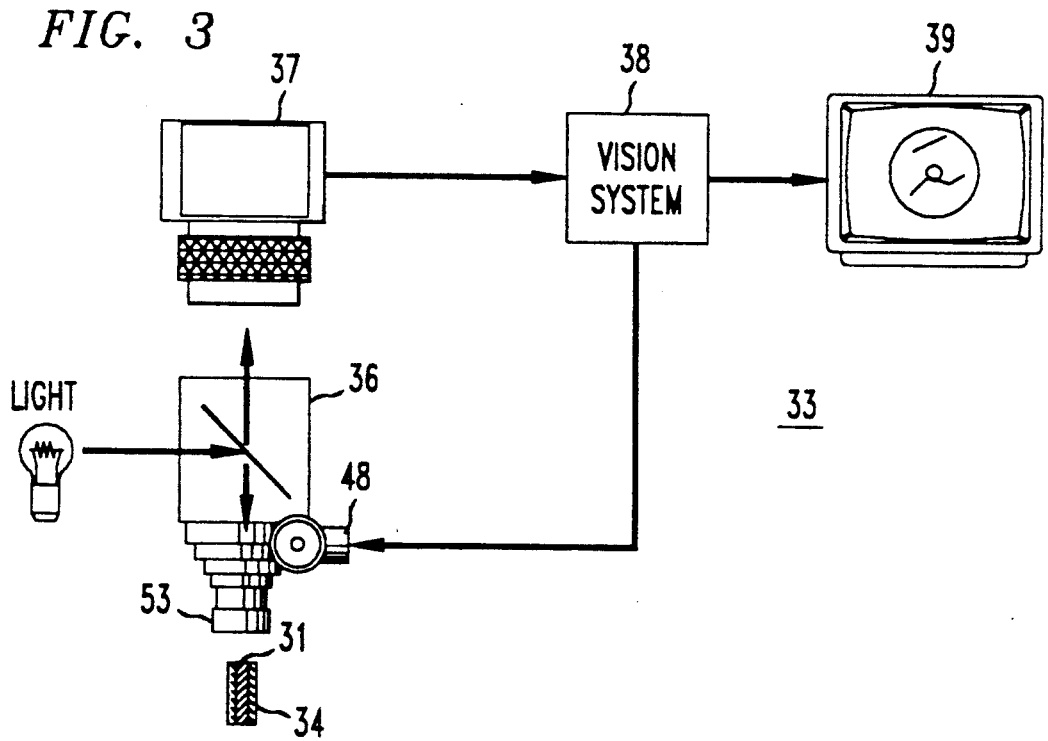
FIG. 3 is a schematic view of a machine vision acquisition, processing and display apparatus which is used to carry out the methods of this invention.

Referring now to FIG. 1 there is shown a flow chart which is designated generally by the numeral 30 and which depicts a method of controlling machine version apparatus to detect features of interest in an end face of 31 of an optical fiber end portion 32 (see FIG. 2). An apparatus which is controlled by the method depicted by the flow chart 30 and which is designated generally by the numeral 33 (see FIG. 3) is used to detect defects, to classify and to quantify the defects in terminated optical fibers. A connector ferrule 34 (see FIG. 2)

which is under test and which terminates the end portion 32 of an optical fiber is placed near the focal point of a microscope 36 (see FIG. 3) and illuminated to enable an image of the end portion of the fiber to be incident on a sensor of a television camera 37. The camera converts the image to an analog signal which is digitized, stored, recalled and processed on a suitable machine vision system 38 (such as that provided by IRI Vision, Matrox, Imaging Technology, Inc., for example) and displayed on a monitor 39. The methods of this invention provide a sequence of steps (algorithm) which are used to acquire images and to process, quantify and interpret the images thus acquired. The algorithm is described hereinafter, is illustrated schematically by subprocess flow charts and facilitates classification based on information acquired from a Region of Interest (ROI).

Figure 4:
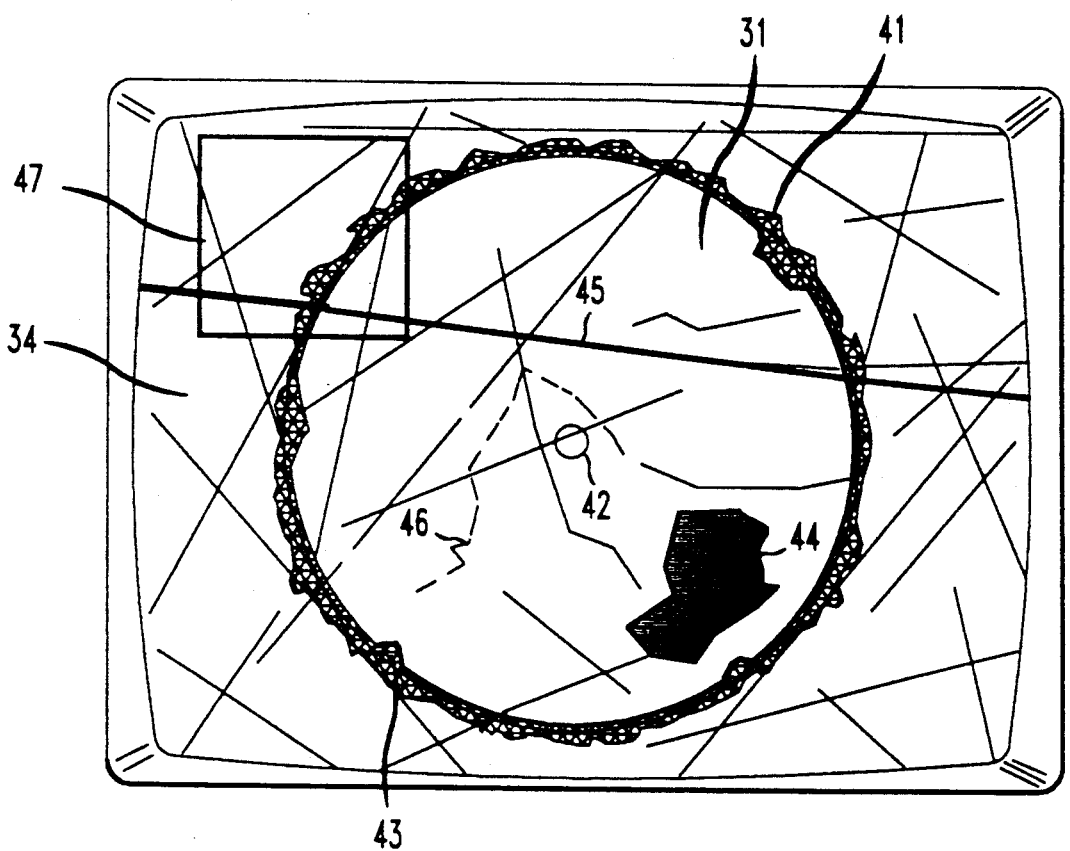
FIG. 4 is a primary or optimum focus image of a terminated end face of an optical fiber having several kinds of defects as the image appears on a monitor of the apparatus of FIG. 3.

A Region of Interest in the reflected light image of the connector ferrule is the end face 31 (see FIG. 2) of a glass fiber end portion 32 which has a circular cross section (see FIG. 4). It should be noted that FIG. 4 depicts an image of the terminated optical fiber end face 31. In figures to follow, it should be understood that images of the end face of the optical fiber are depicted. Also, it should be noted that the lines shown in the images herein are intended only to illustrate contrast to the background, and are not intended to represent grey scale levels of intensity as is typical of machine vision imaging. A thin band 41 (see again FIG. 4) of epoxy disposed between the fiber and the surrounding ferrule 34 to hold the fiber secured within the ferrule is an artifact formed during the polishing of a protruding portion of the optical fiber end portion 32.

Possible defects in the end face of the optical fiber can be classified into several different categories based on their properties. Chips 43—43 (see again FIG. 4) are voids in the end face surface which extend to the boundary of the fiber. When illuminated by incident white light from a microscope, chips appear darker than the surrounding smooth fiber surface. Pits 44—44 are voids which occur inside the fiber and are completely enclosed by the material of the fiber. Sometimes a polishing process causes a shard of material to roll across the surface and create an array of pits along a line. These are called digs. (not shown). Digs will not be discussed further herein inasmuch as the detection of pits necessarily by definition identifies digs.

Polishing generally involves the use of an abrasive material to remove material of the fiber. The path left by an abrasive material is usually a straight line referred to as a scratch 45 (see FIG. 4). Successive polishing steps produce smaller and smaller scratches until a desired degree of surface finish is obtained. Sometimes, defective or contaminated polishing media form a new scratch in a smooth surface. Scratches are usually very straight, and have a higher average intensity than the surrounding area. Scratches may be only a few nanometers deep but constitute a cosmetic surface defect. On the other hand, cracks such as a crack 46 shown in FIG. 4 comprise a separation of the material of the fiber, and have the unique property that their intensity profile changes considerably when viewed slightly above or below a focal plane. Cracks in fiber end faces are usually curved and may branch, have essentially zero width and may not be visible when viewed in-focus under high magnification. The structure or presence of a crack often becomes apparent if the microscope is slightly out of focus. Cracks pose a problem because over time they can propagate and cause the optical fiber to fail.

Defects of the kind just described are detected and quantified by methods of this invention. The flow chart 30 which is shown in FIG. 1 depicts the general steps of the method. As is seen in FIG. 1, image acquisition is followed by fiber isolation. Then, chips, and pits are detected and classified. Scratches and cracks also are detected and quantified after which a decision may be made as to the acceptability of the polished ferrule. The method as exemplified by the flow chart of FIG. 1 may be divided into subprocesses and these are described in flow charts which follow, together with the description herein.

The quality of the images on which the classification is performed is important to the results. Image quality is governed by lighting and focusing. Because of the small size of optical fibers, that is, an eight micron size core 42 (see FIG. 4) for single mode fibers, for example, their visual inspection requires the use of a microscope.

An image is represented by an array of picture elements, commonly known as pixels, which may vary in intensity value from 0 to 255, for example, where 0 is black and 255 is white and levels therebetween are referred to as grey levels. Variability in lighting conditions can be compensated for during processing by adjusting the parameters based on a grey-level histogram, which shows the frequency distribution of intensity of pixels which comprise the image. On the other hand, the variability in focusing can lead to different results and is difficult to deal with once the image has been acquired. Problems of variability in focusing stem from the extremely limited depth of focus of images acquired under high magnification. The lack of repeatability when the focus position is determined manually leads to inconsistent results when the same optical fiber is focused on repeated occasions. Secondly, it has been found that different features of interest exist at different planes of focus. As a result, it appears impossible to obtain one image in which all of the features of interest are in sharp focus.

The first problem is solved by the use of an automatic focusing arrangement. The second problem is overcome by obtaining images at several different focus settings and fusing the information into a single image.

Acquisition of Images Through Automatic Focusing and Multiple Image Fusion

Figure 5:
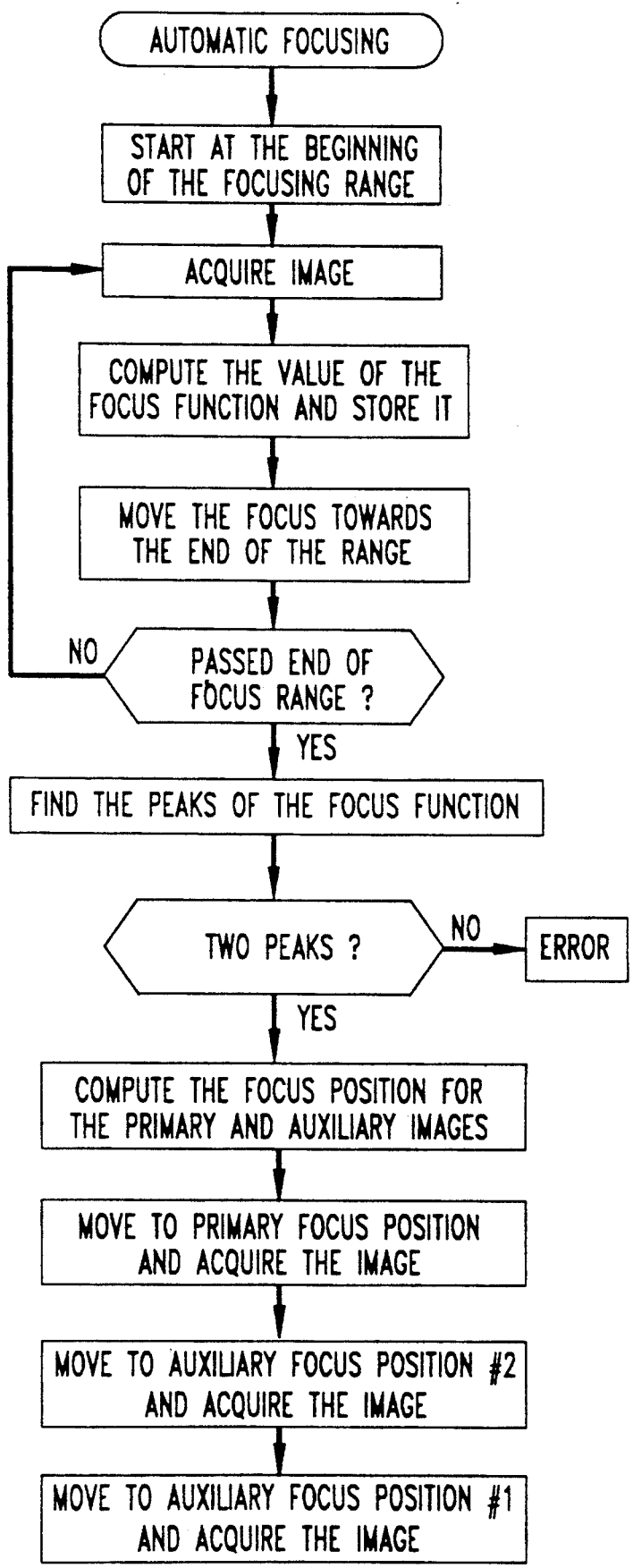
FIG. 5 is flow chart which depicts a subprocess of automatic focusing and image acquisition.
Figure 6:
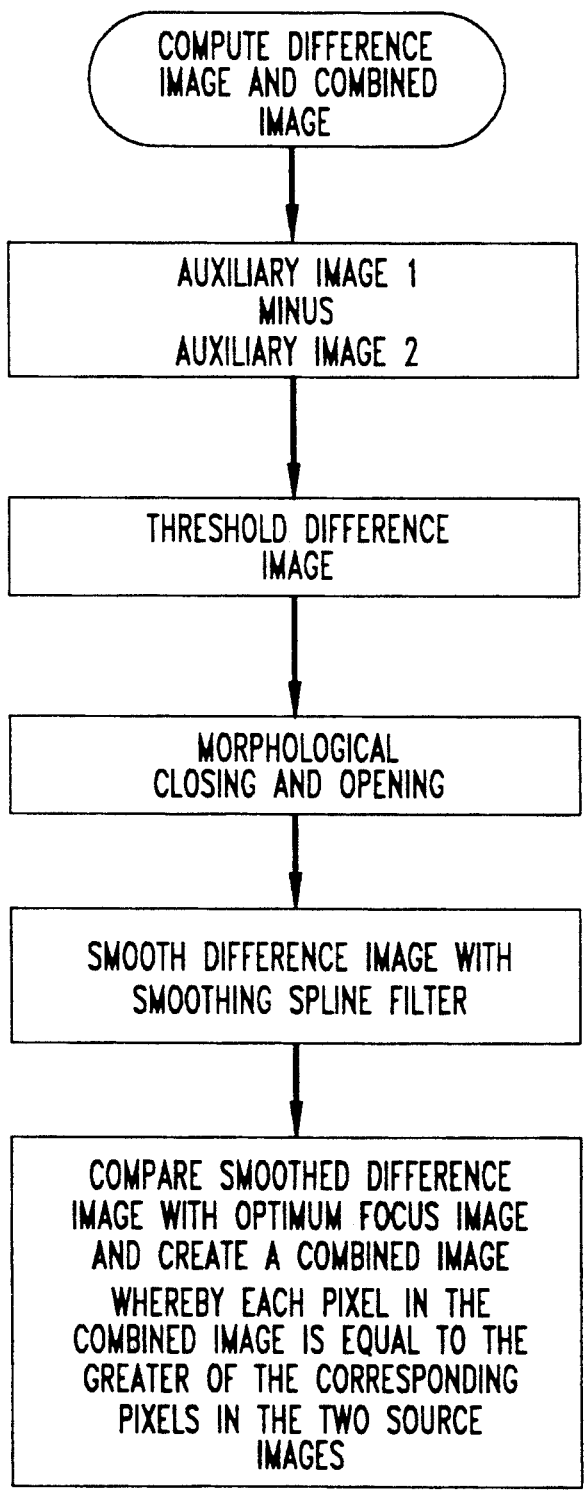
FIG. 6 is a flow chart which depicts the generating of a difference image and of a combined image.

The acquisition and processing of images through automatic focusing and multiple image fusion are depicted in flow charts shown in FIGS. 5 and 6. Prior art automatic focusing methods usually involve finding a single focus position for acquiring an image. In the case of optical fiber connectors, this is not suitable because a single focus position does not convey sufficient information about all the features of interest in an end face of the optical fiber.

Automatic focusing is accomplished by computer control of the microscope focus. A microscope focus mechanism 48 (see FIG. 3) is provided with a stepper motor which is capable of being controlled by a machine-readable program. The sharpness of the focus is measured by a metric referred to as the focus function.

It has been determined that focus functions based on intensity gradient lead to the best results. A gradient function at each pixel is computed using gradient operators which generate estimates of the first derivative of the intensity function in horizontal and vertical, i.e., x and y, directions. These two derivatives are assigned a threshold to reduce the effects of noise and are used to compute a sum of squares of gradient values, hereinafter referred to as the focus function.

The focus function so determined for the terminated fiber used herein is bimodal. By acquiring a multiplicity of images in the vicinity of the focus position of the microscope and computing a suitable focus metric in a Region of Interest 47 (see FIG. 4), a number related to the high frequency content of the image can be obtained for each focus position. Plotting this resultant against focus position of the microscope results in a twin-peak focus function shown in FIG. 7. The focus function obtained herein includes two closely spaced peaks 51 and 52 (see FIG. 7). The curve of FIG. 7 is a plot of the sum of the squared gradients in the ROI 47 which is scrutinized versus the vertical distance of the lens from the area.

The sum of the squared values of the intensity gradient shows the rate of change in intensity as a small area is scrutinized. For a blurred image, the rate of change in intensity will be low; for a sharper image, the gradient adds to a larger number.

The image includes features which appear at different focal planes. Accordingly, to compute the focus function on the entire image affects adversely the focus function. A better approach is to base the computation on a smaller portion of the image. It has been determined that using a small region of the image, based on a matrix typically of 100×100 pixels (e.g. ROI 47 in FIG. 4) on a portion of the ferrule 34 surrounding the fiber, which may be a ceramic material, for example, provides acceptable results.

Figure 7:
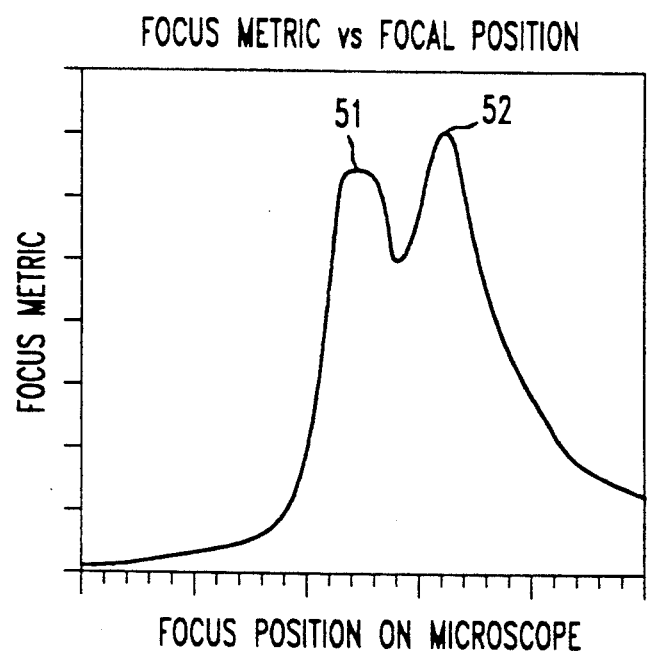
FIG. 7 is a graph of a focus metric versus focus position of a microscope of the apparatus of FIG. 3.

When looking at the ferrule material surrounding the fiber under a microscope, scratches come into sharp focus at two distinct positions which are the positions at which the peaks 51 and 52 appear in FIG. 7. The position which is referred to as the optimum focus position and which is at or near to the plane of the end face of the connector and at which scratches on the surface of the fiber come into sharp focus does not coincide with either of the peaks of the bimodal function. However, this optimum focus position has been determined empirically based on the location of the two peaks by observing a large number of terminated optical fibers. In most cases, images obtained at this optimum focus position do not provide sufficient information about cracks.

As mentioned hereinbefore, the limited depth of focus of a microscope presents problems in obtaining images with sufficient information about all features of interest. In most cases, it is difficult to distinguish between cracks and scratches based on a single image. Cracks are deeper than scratches and affect the optical properties of glass differently. Also, because illumination is accomplished by a beam passing through an objective lens 53 (see FIG. 3) of the microscope, a change in focus positions also tends to modify the illumination. Hence, cracks exhibit a much larger depth of variation in grey level under changes in focusing. This property may be utilized to detect cracks and to distinguish them from scratches.

Figure 8:
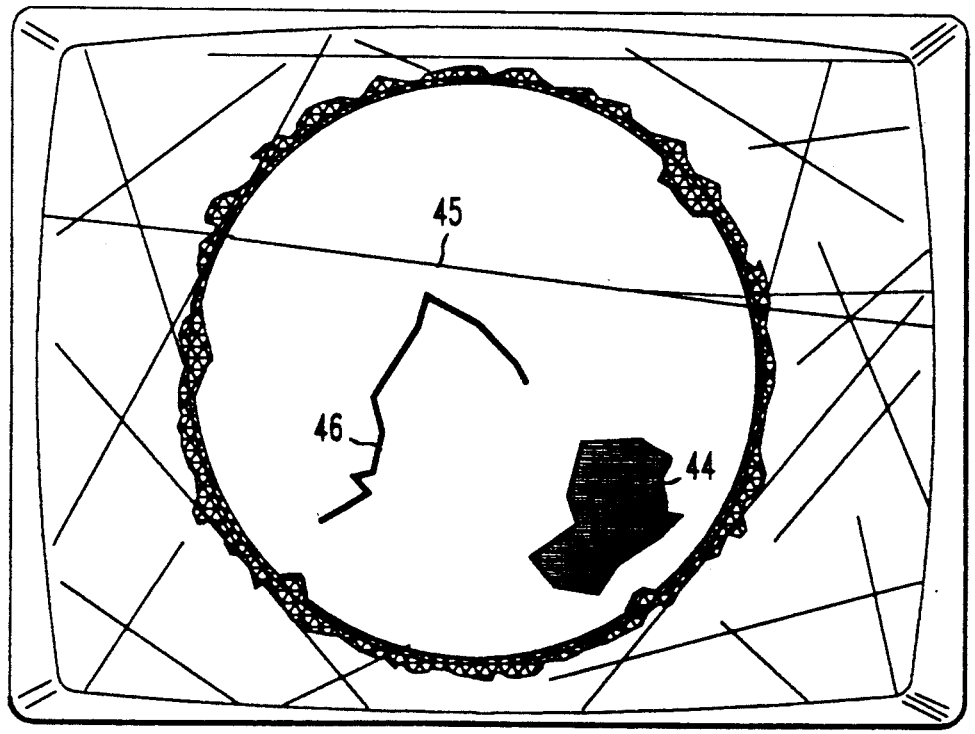
FIG. 8 is an image of the end face of the terminated optical fiber as acquired at an auxiliary position.

After an optimum focal position for scratches has been determined empirically from the dual peak focus function curve of FIG. 7, the focus function is used to determine two auxiliary focal positions on opposite sides of the optimum position. One image obtained at the optimum focus position and which is the best focus image on a grey scale, is referred to as the primary image and is shown in FIG. 4. Two images acquired at auxiliary focus positions in front of and behind the optimum focus position on a grey scale are referred to as the auxiliary images and are used to generate a single image. For the arrangement shown in FIG. 3, the auxiliary images are acquired above and below the primary image. An example of an auxiliary image is illustrated in FIG. 8. As can be seen by comparing FIGS. 4 and 8, the scratch 45 is visible in FIG. 4 but is out of focus in FIG. 8 whereas the crack 46 is subdued in the primary image in FIG. 4 but is very visible in FIG. 8.

Figure 9:
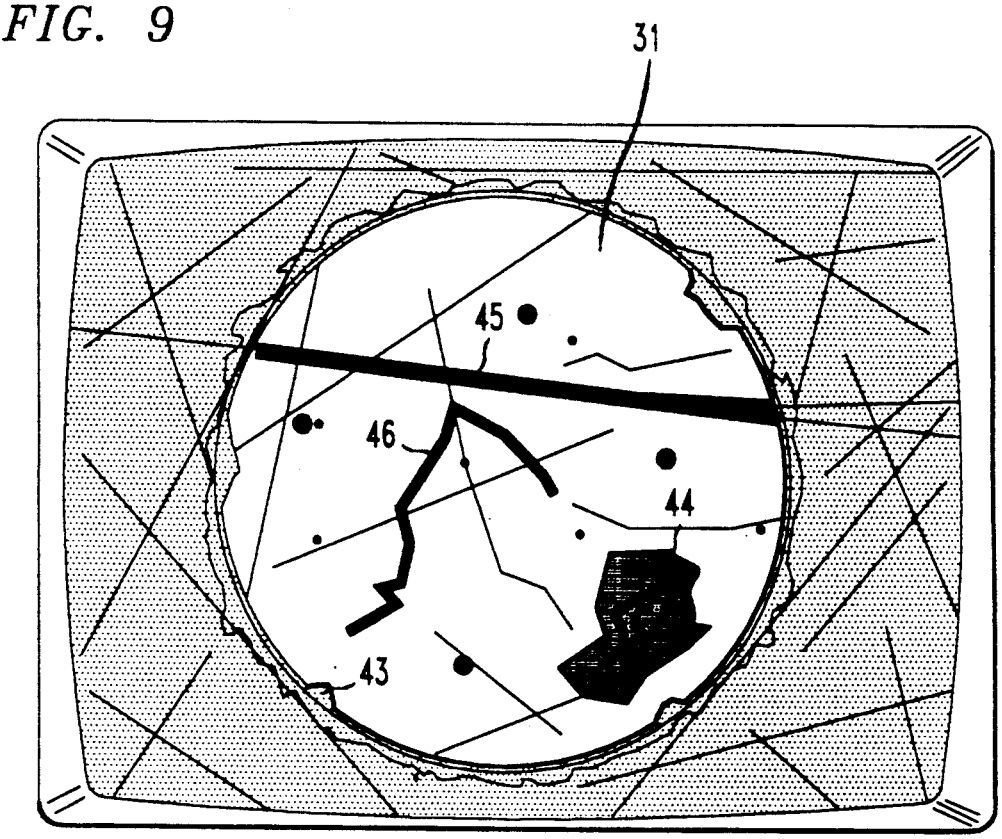
FIG. 9 is a view of a combined image.

All subsequent processing steps are performed on one or more of these images, or on intermediate images resulting from processing one, or two or all three of the original images. For example, all three images are combined in such a way as to create a so-called combined image (see FIG. 9) which carries information which enables detection of both cracks and scratches. This usually is not possible with a method that uses only a single image.

Another image, the so-called difference image, is formed by computing the absolute value of the difference between the two images which have been acquired at the auxiliary focus positions on a grey scale. As will be recalled, the acquired image is represented by numbers. As a result, portions of the acquired image can be accepted or rejected based on whether numbers which represent each area are larger or smaller than desired values. This is referred to as thresholding. The difference image is thresholded to eliminate small differences which result from minor variations between the two images.

Figure 10:
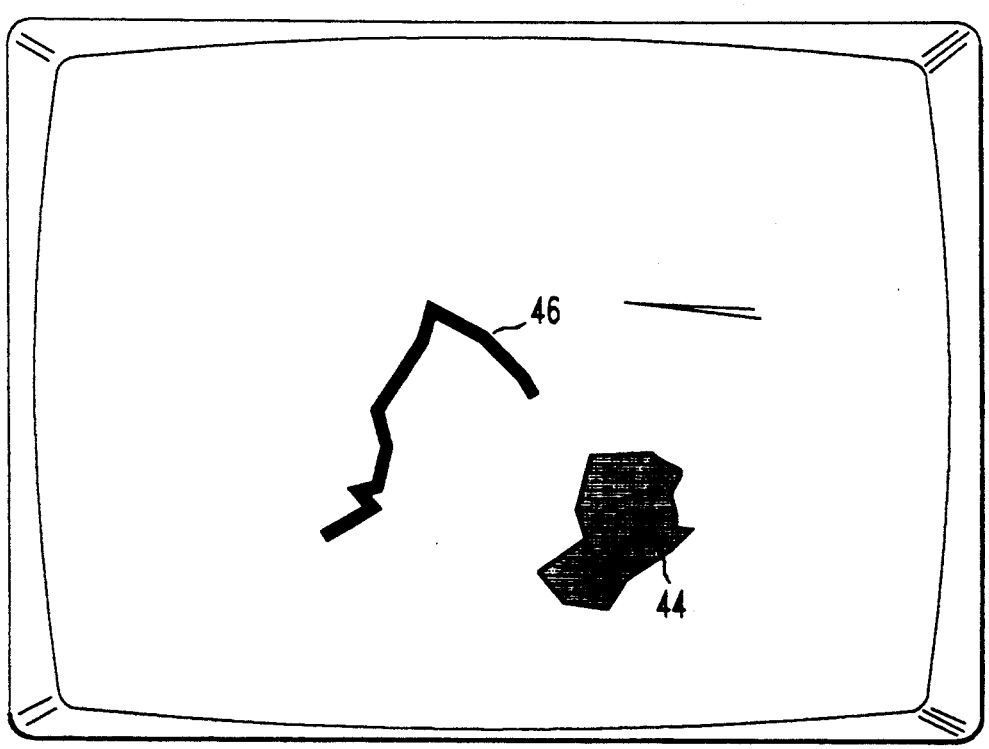
FIG. 10 is a view of a binary difference image.

The difference image generated after thresholding is referred to as the binary difference image and is refined further through morphological closing followed by opening, both with disc-like structuring elements. See "Defect Detection, Classification Quantification in Optical Fiber Connectors: authored by B. Shahraray, A. T. Schmidt and J. M. Palmquist which was presented during the Nov. 28-30, 1990 workshop in machine vision applications. In this procedure, the size of the discs is chosen such that components within a predetermined distance are merged and components under a predetermined size are eliminated (see FIG. 10).

The difference image includes blobs related to real surface features as well as other, small, generally isolated blobs related to noise in the image. A blob is machine vision parlance for any group of pixels which are connected together. It is desired that significant blobs be retained while those related to noise are discarded. This is accomplished by morphological closing followed by opening. The difference image is first closed to join adjacent blobs and then opened to eliminate noise. In general, closing will cause closely spaced blobs to join together. Opening on the other hand causes weakly connected blobs to become separated and certain smaller blobs to disappear entirely.

Dilation with a disc is accomplished as follows. A disc-like structuring element is located with its center at each possible pixel position in the image or ROI. If any element of the image corresponding to a portion of the disc is non-zero, then the pixel of the image corresponding to the center pixel of the disc is set to a non-zero level. This causes boundaries of blobs to grow.

Erosion is accomplished as follows. The disc-like structuring element is again located with its center at each possible pixel position of the image or ROI. If all the pixels in the image which correspond to disc pixels are non-zero, the pixel of the image corresponding to the center pixel of the disc is set to a non-zero value. Otherwise, the center pixel is set to zero. This causes blob boundaries to shrink and very small or narrow blobs to disappear.

Opening with a disc is accomplished by performing an erosion by the disc followed by dilation with the same disc. Closing with a disc is accomplished by dilation with the disc followed by erosion with the same disc.

The processed difference image then is smoothed by a low pass filter having a gain, G, to cause the binary image then to be converted into a grey scale image, i.e. to go from a sharp intensity profile to a generally gradually changing intensity. In smoothing, a binary image, i.e., black and white, is blurred by low pass filtering. Instead of a sharp intensity profile, a slowly varying bell-shaped intensity profile is obtained. The gain, G, is chosen such that it brings the intensity of the generated image to typical levels of scratches. Further, the low pass property of the filter generates a decreasing intensity profile which gradually approaches a zero background. This results in an image which is referred to as a processed difference image. The processed difference image is a grey scale image of the binary difference image after morphological closing and opening followed by smoothing with a gain to obtain an intensity comparable to that of scratches. The processed difference image highlights the cracks and may also include information about the boundaries of chips and pits.

The combined image (see FIG. 9) is formed by setting each pixel to the larger of the values of the corresponding pixels in the primary image and in the processed difference image. As a result, most of the pixels in the primary image are retained and stored, whereas regions where cracks occur are replaced by grey-scale difference images. The combined image includes scratches and cracks. Afterwards, edge detection is performed on this image. The binary difference image (see FIG. 10) is retained for later use in discriminating between cracks and scratches.

Fiber Isolation

Figure 11:
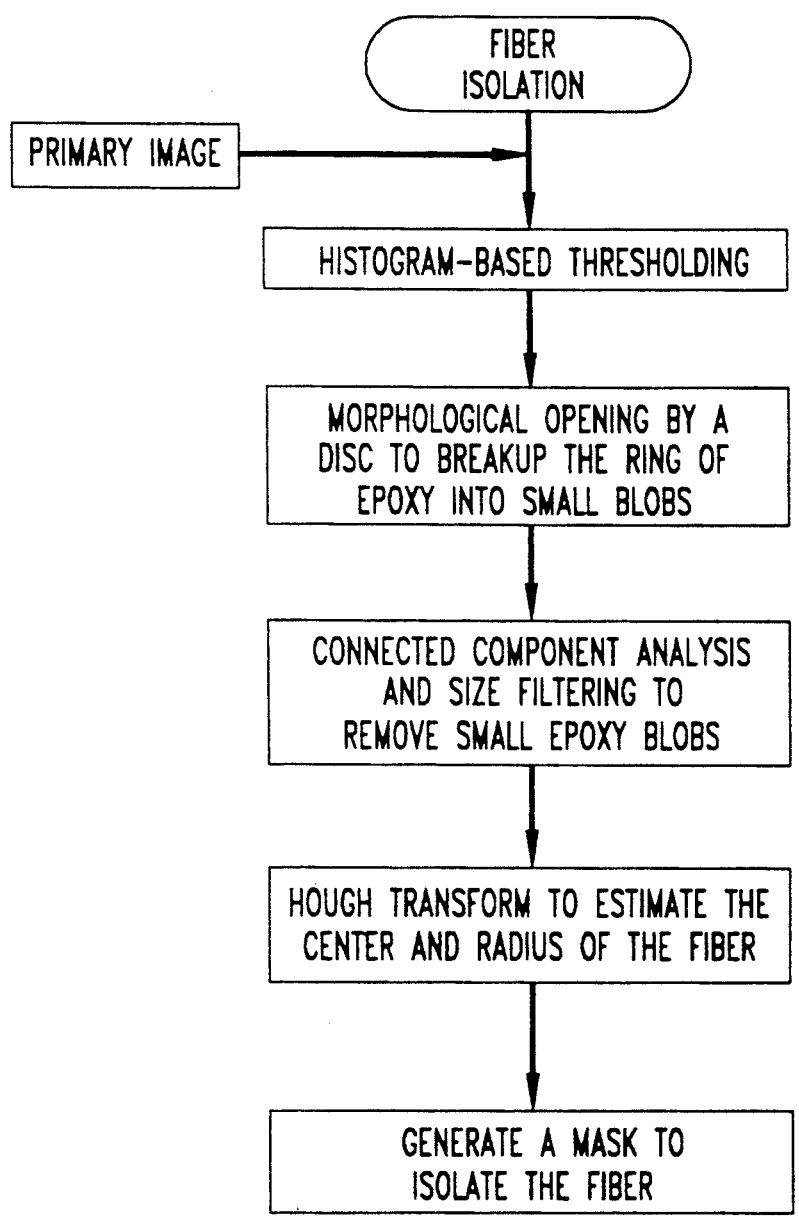
FIG. 11 is a flow chart of the isolation of the end face of the optical fiber in an acquired image.

Following image acquisition, the method includes the general step of fiber isolation, the flow chart for which is depicted in FIG. 11. The image includes information about the fiber end face 31, as well as of surrounding background material of the optical fiber ferrule 34. Because the fiber end face 31 (see FIG. 4) is the region of interest to be analyzed, it must be isolated from the background.

Figure 12:
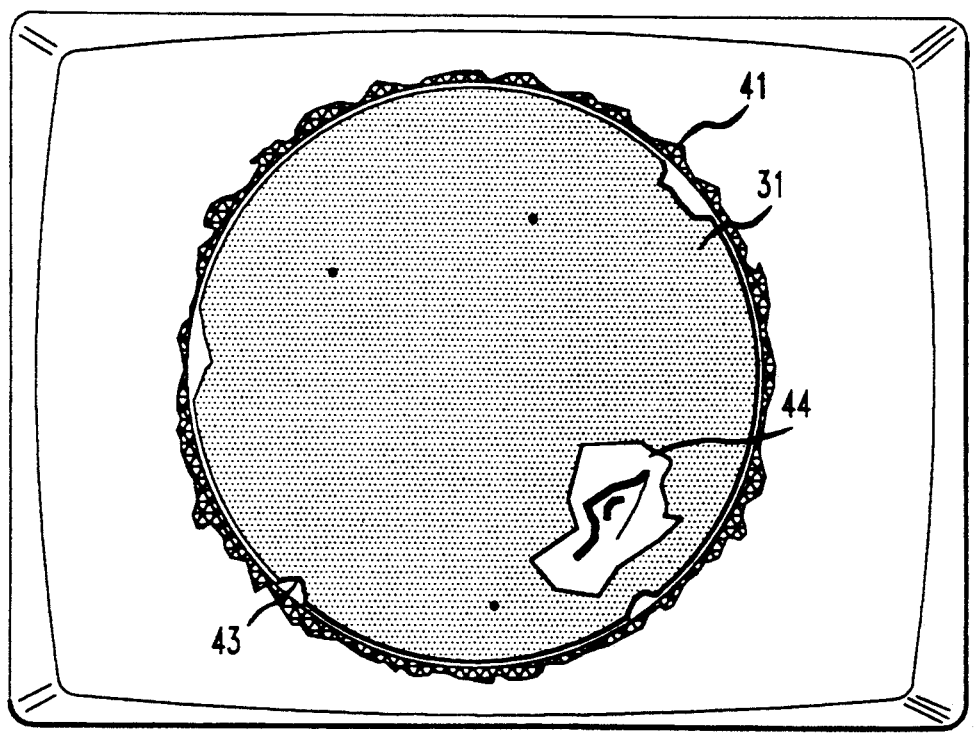
FIG. 12 is a view of the combined image of FIG. 9 after thresholding for fiber isolation.
Figure 13:
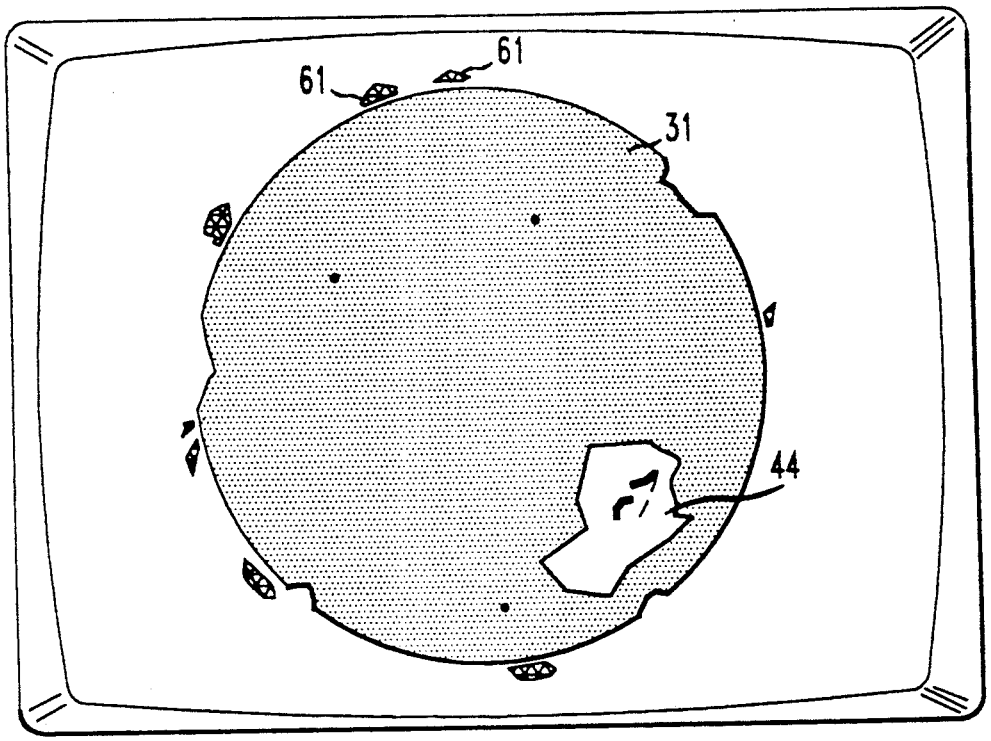
FIG. 13 is a view of the image of FIG. 4 after thresholding and after morphological processing by opening with a disc.

The optimum focus or primary image is thresholded using limits calculated from analyzing the intensity distribution of the primary image i.e., intensity histogram of the primary image (see FIG. 11). The resulting binary image (see FIG. 12) then is opened morphologically using a structuring element (typically a disc) which causes the optical fiber portion of the image to become separated from the surrounding area (FIG. 13) and also to break up of the ring of epoxy 41 into smaller regions or blobs 61—61.

Figure 14:
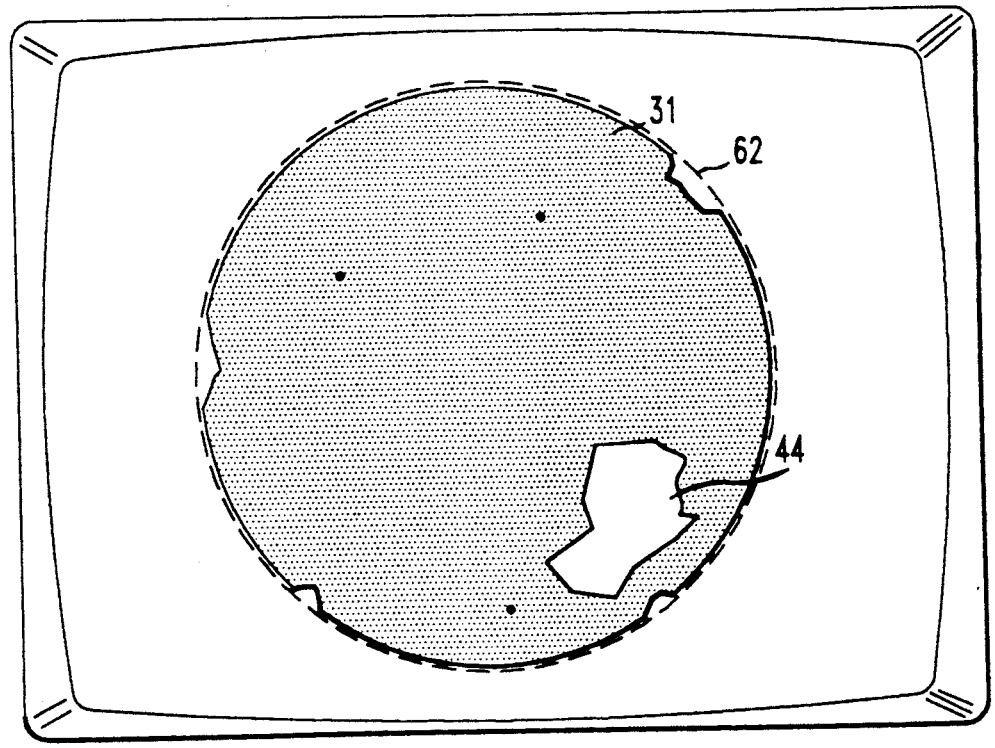
FIG. 14 is a view of the image of FIG. 13 after size filtering of blobs.

As used hereinbefore, the expression "opened by a disc" means that whenever blobs are large enough for the disc to be received in the blob, the portion of the blob corresponding to the center of the disc is retained. If it isn't, the portion corresponding to the disc is discarded. This amounts to a size filtering process. The ring of epoxy 41 which is used to secure the optical fiber within a passageway in the ferrule may have grey levels similar to that of the optical fiber. Further, some of the features on the ferrule 34 have grey levels in the same range as the fiber. The image in FIG. 13 now includes blobs 61—61 which are analyzed for area and discarded if they are below the size threshold for a fiber. The unwanted regions are eliminated by performing connected component labeling, computing the size of each connected component and eliminating those which are small (see FIGS. 12, 13 and 14). In connected component labeling, each pixel is examined to determine if it has a non-zero neighbor and if it has, the two are assigned the same label. In other words, each set of connected pixels are assigned the same label and are considered to be an individual blob. Then the image is thresholded to discard those blobs having a pixel count, i.e., area, below a predetermined value. FIG. 14 shows the image after small blobs have been discarded. Note that the fiber end face itself is a large blob and is retained.

The image obtained from the portion of the process depicted in FIG. 11 and discussed thus far is often not a perfect disc for two reasons. First, the process can include either part of the background or can be such as to remove a defective portion of the fiber having a significantly different intensity. Second, chips can cause portions of the fiber boundaries to appear missing. In these cases, the result of the process thus far is a partial disc with imperfect and partial boundaries, as illustrated in FIG. 14.

The most probable location of the optical fiber is found by applying a two dimensional Hough transform to the isolated fiber blob image (of FIG. 14) to locate the set of points having the most probable center location and radius. A circular mask 62 (FIG. 14) then is created and can be applied to any of the acquired or processed images to separate the optical fiber from the background.

It is known that a perpendicular bisector 65 (see FIG. 15) of every chord 66 of a circle 67 passes through a center 68 of the circle. In order to find the center of the circle, it is sufficient to find the intersection of the perpendicular bisectors 65—65 of two non-parallel chords. Once the center has been found, the radius can be obtained by computing the distance of the center 68 from any point on the circle. Given a disc with noisy and imperfect boundaries, this property can be used to estimate its center by considering a large number of pairs of points on the boundary and computing the perpendicular bisectors of the chords which extend through the pair.

A two-dimensional accumulator 69 (see FIG. 15), discretized to the resolution of the image and limited to a rectangle about the center of the image, can be used to record the intersection points of the bisectors. Given a sufficient number of acceptable points on the boundary of the circle, an estimate of the center can be obtained by finding that accumulator cell which has a maximum number of votes.

A similar voting scheme then can be used to estimate the radius by incrementing a one-dimensional discrete accumulator based on the distance of each boundary point from the estimated center. The value associated with the accumulator cell with the maximum number of votes is the estimated radius of the circle. When applying the algorithm just described, acceptable estimates of both the coordinate of the center and the radius of the fiber, are generated.

Figure 15:
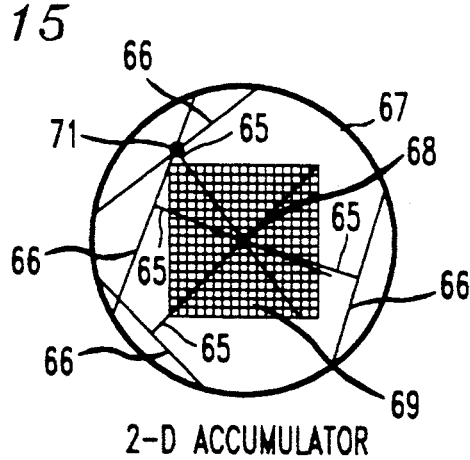
FIG. 15 is a view of a two dimensional arrangement for the accumulation of votes to determine the center of an end face of optical fiber.

A point 71 inside the fiber, which is closer to the boundary than to the center of the fiber, can be used to generate a number of uniformly spaced rays or chords 66—66 (see FIG. 15). Each ray is traced from its origin inside the circle to points of intersection with the image boundary. The two points found in this way are taken as points on the boundary of the image and are used to compute the perpendicular bisectors 65—65 of the chords 66—66.

The above-described method can be made more robust by using more than one point as the source of rays used to obtain the chords. This will help reduce the possibility of generating too many unacceptable chords when the source of rays happens to be close to part of the boundary having a major defect. Considerable reduction in computational complexity of the method can be made by restricting the rays to horizontal and vertical directions. This will cause the rays to coincide with the rows and columns of the image, and leads to major simplifications in computing the bisectors.

Because horizontal and vertical chords can vote only for x and y coordinates of the center, respectively, two one-dimensional accumulators (see FIGS. 16 and 17) are used instead of a two-dimensional accumulator. It should be pointed out that the reduction in the computational complexity is at the expense of robustness. When using rays of arbitrary direction generated from several points, the method is capable of dealing with distortions which alter a relatively large portion of the boundary.

Figure 16:
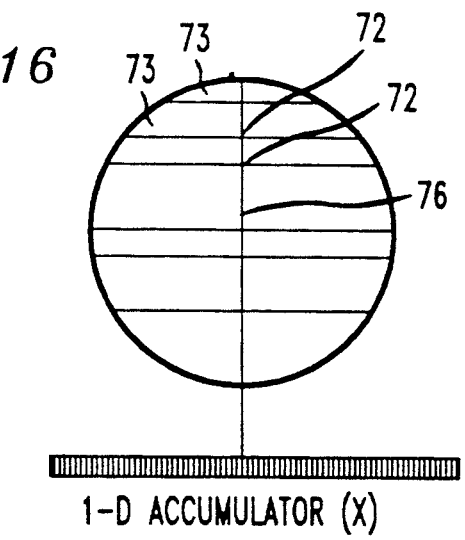
FIGS. 16 and 17 are views of two one-dimensional arrangements for the accumulation of votes to determine the center of an end face of a terminated optical fiber.
Figure 17:
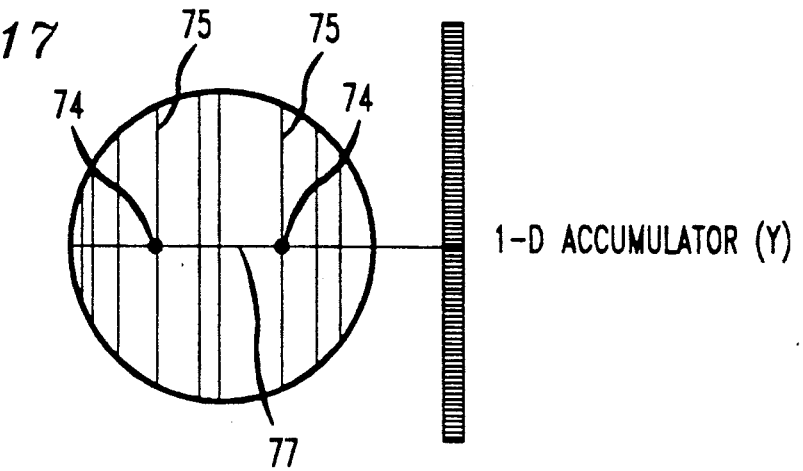

In the method of this invention, the binary image in FIG. 14, in which the fiber end face is white and the area outside thereof is black, is scanned left to right and right to left to determine the boundaries of the fiber and to find a center point 72 between the two fiber boundary points on each horizontal line scan 73 (see FIG. 16). Then the image is scanned top to bottom and bottom to top (see FIG. 17) to determine the boundaries of the fiber and to find a center point 74 between the two fiber boundary points on each vertical line scan 75. Scanning in two directions in both horizontal directions instead of continuing in one direction horizontally and vertically avoids the problem of encountering a pit which would give a false indication of a fiber boundary. The intersection of two lines 76 and 77 (see FIGS. 16 and 17) which join the centers from horizontal scan lines and from the vertical scan lines, respectively, is the center of the fiber. Then the distance from the center to each boundary point is calculated to determine the radius. The radius is set to correspond to that distance which occurs most often.

The algorithm does not use information about the radius of the fiber. However, once the radius has been estimated, it is compared against typical radius values. A large discrepancy is indicative of a major problem with the fiber and is used to terminate the process.

The estimates of center and the radius of the fiber are used to isolate the fiber by using a circular mask 62 to clear all the image pixels outside the fiber. The size of the image is reduced so that is includes only the fiber end face 31 and a border sufficient to allow performing neighborhood operations on the image (see FIG. 14).

Chip and Pit Detection and Quantification

Figure 18:
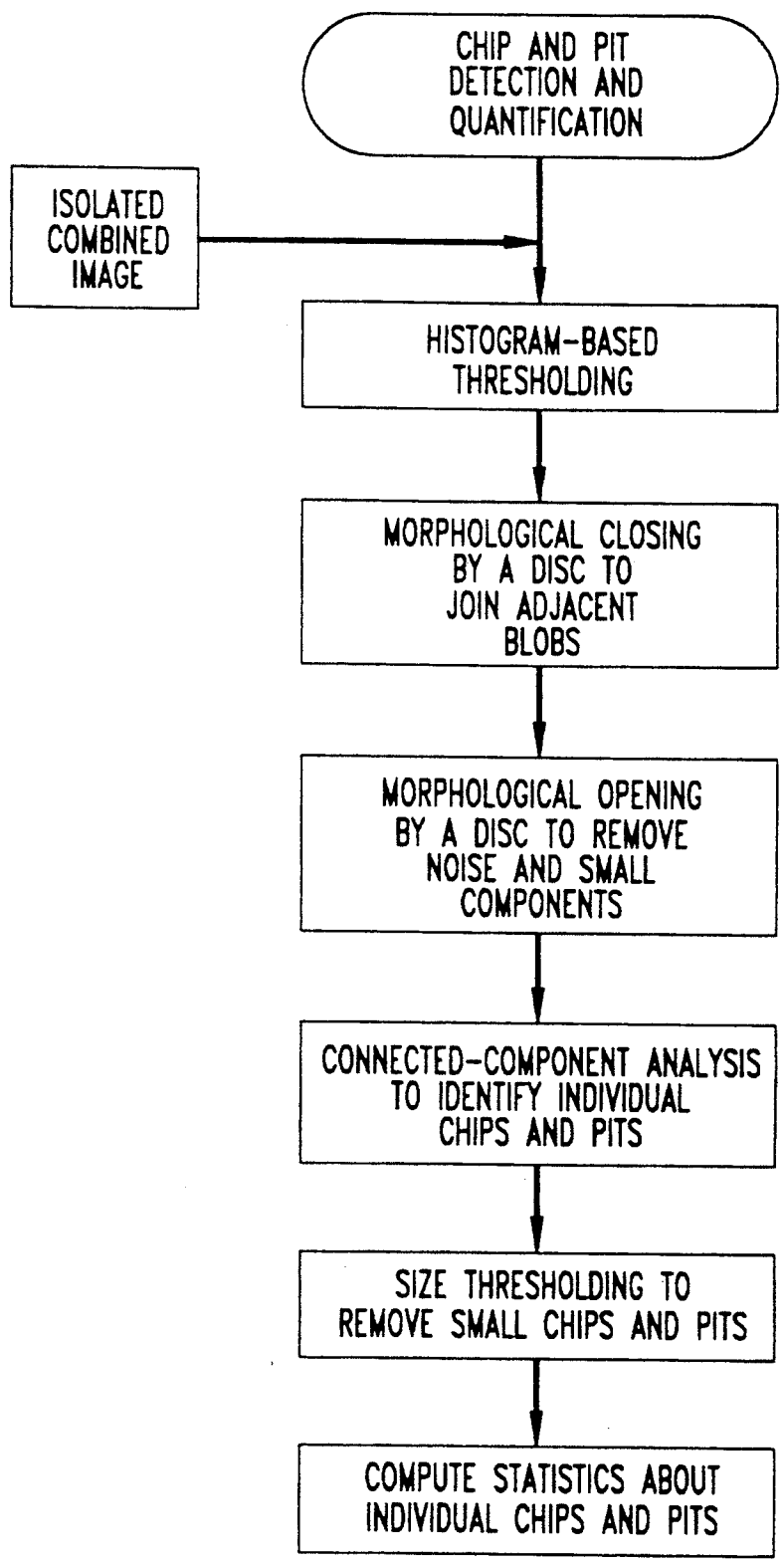
FIG. 18 is flow chart of a subprocess for the detection and quantification of chips and pits in an end face of a terminated optical fiber.
Figure 19:
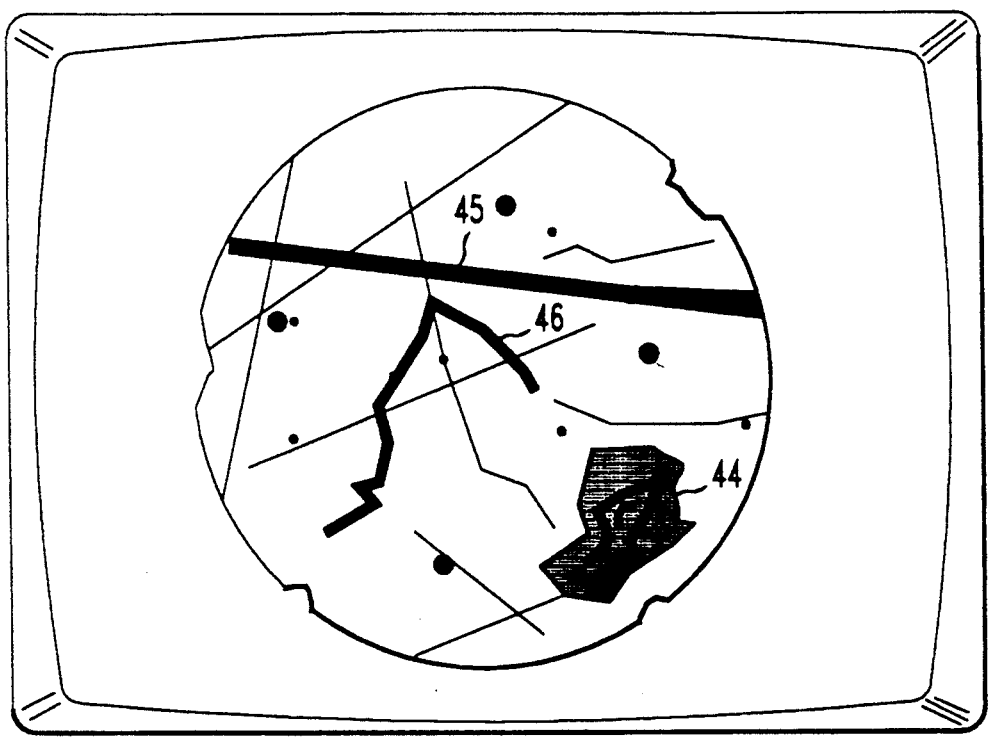
FIG. 19 is an image of the isolated optical fiber portion of the combined image.

A flow chart which depicts a subprocess for the detection and quantification of chips and pits is shown in FIG. 18. The circular mask 62 (see FIG. 14) provided during the fiber isolation portion of the method is combined with the primary image to provide a new image containing only the fiber portion of the combined image, surrounded by pixels of level zero (FIG. 19).

Among the possible defects on the polished surface of the optical fiber, chips and pits are the easiest to detect. These defects manifest themselves a regions in the primary image with intensities which are markedly different from other portions of the fiber. As a result, they can be separated by thresholding.

Figure 20:
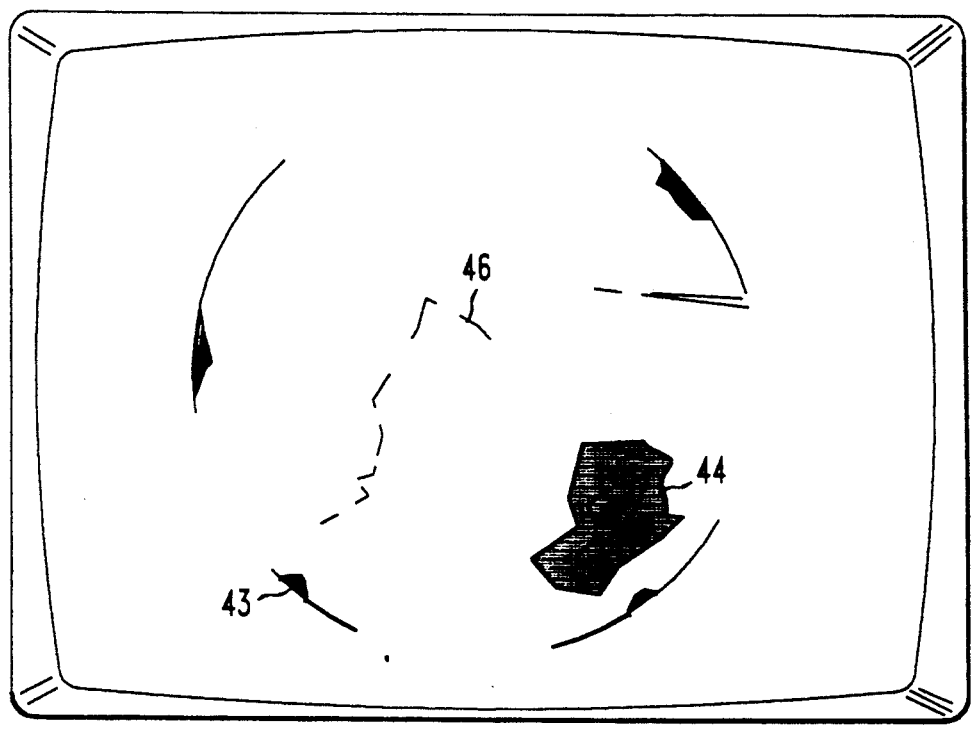
FIG. 20 is a view of the combined image thresholded for chips and pits.

The intensity histogram for the isolated optical fiber is used to determine the range of grey levels for the fiber. Thresholding is used to separate the regions outside this range. The image is histogram-thresholded in such a way as to cause areas which differ in intensity from the mean $\pm 1\delta$ (standard deviation) of the fiber background level to appear white, i.e., non-zero grey level, whereas the surrounding fiber is set to zero. The image obtained in this way includes additional unwanted features caused by noise, scratches and cracks (see FIG. 20). Further, an individual chip or pit may be broken into several portions because of intensity changes within the chip or pit region. A morphological closing technique which has been described hereinbefore and which employs a disc structuring element is used to merge close segments and fill small holes inside the detected regions. The resulting image is then opened by a disc. The size of the disc is adjusted such that it is sufficiently large not to fit inside the segments resulting from cracks, scratches and small regions which are due to noise. The opening technique discards the scratches and cracks because of their limited thickness. It also performs size filtering by discarding chips which are below a certain size threshold determined by the size of the disc structuring element used.

Connected component labeling is used to mark individual chips and pits. Further, size filtering is performed by computing the size of each component and deleting those below a predetermined size threshold. The resulting image (see FIG. 21) which is provided as an input to the connected component labeling stage is also retained for use by in a scratch/crack detection subprocess. Various statistics about chips and pits such as size, center of mass, distance of center of mass from the core and minimum distance from the core then are computed.

Detection of Scratches and Cracks

Figure 22:
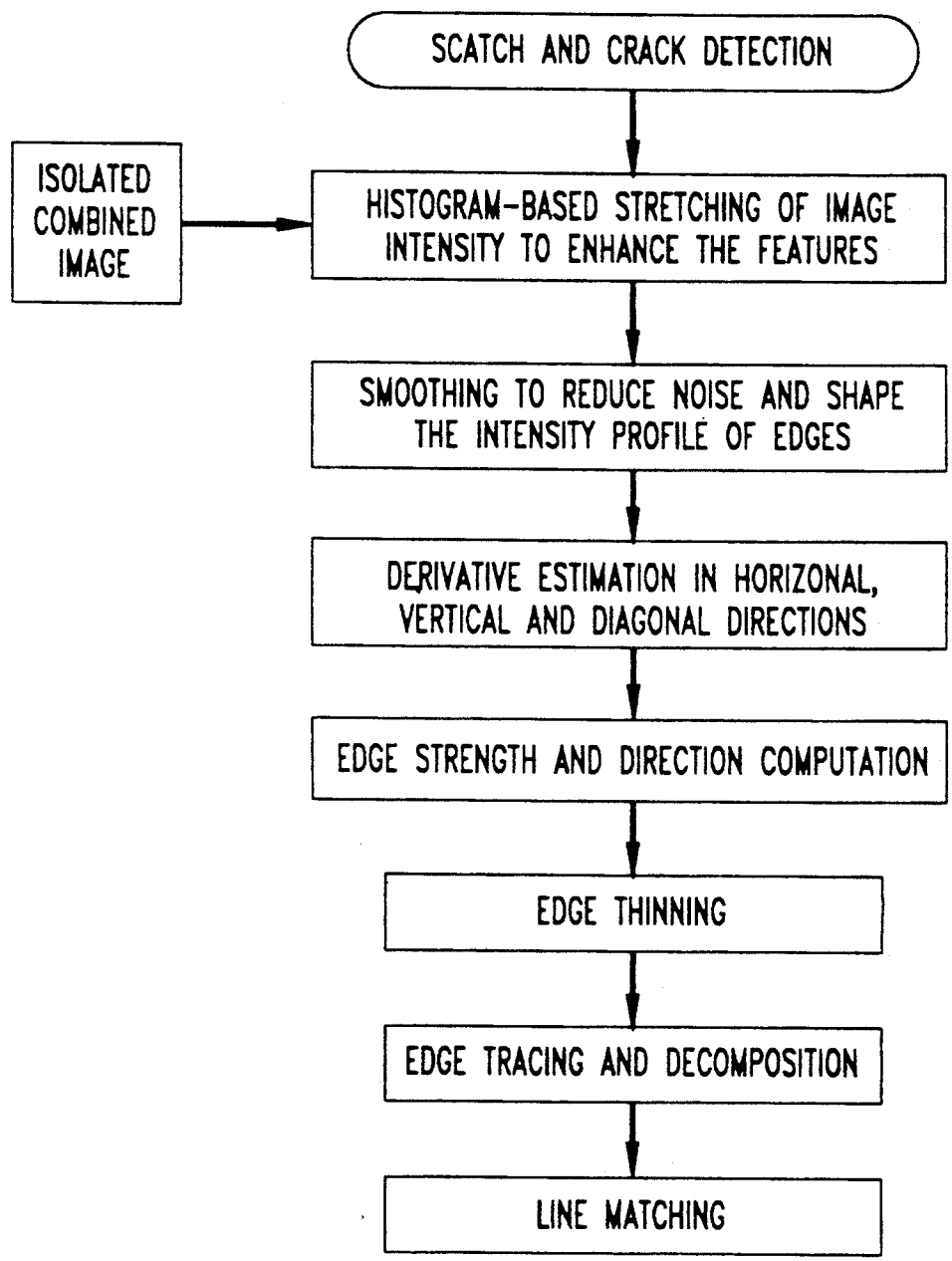
FIG. 22 is a flow chart which depicts the subprocess of scratch and crack detection.

In FIG. 22 appears a flow chart which depicts a subprocess of the method which is used to detect scratches and cracks. Because of the difficulty in detecting fine scratches and cracks with insufficient contrast, a specialized edge detection technique is used.

Because quantification rather than detection alone is needed, steps must be taken to insure consistency of measurements under variations in imaging conditions. First, the histogram for the isolated combined image of FIG. 19 which, as will be recalled comprises the primary image combined with the smoothed difference image is used to determine the range of interest. The image intensity values in the given range are then stretched to fill the entire range. Image intensity values below and above the range of interest are set to the minimum and maximum values, respectively. This allows consistent measurements without adjusting the parameters in subsequent stages of processing. The stretched image is smoothed to reduce noise and to shape the intensity profile of the edges.

Given a scratch, for example, of finite width in the combined image, it is desired to find an edge located at the center (along the width) of the scratch. The maxima of the second order derivative of intensity is used to locate these edges. This is achieved by applying local operators to estimate the derivatives along four directions, i.e., horizontal, vertical and two diagonal. The direction of the scratch can be determined by determining how the derivative changes. The smoothing operation serves two purposes. First, it reduces the effects of high frequency noise. Second, if there are scratches with a flat intensity profile (caused by sensor saturation, quantization, wide scratches, for example), smoothing will convert them such that their intensity profile is bell-shaped. This will enable the derivative operators to generate a peak corresponding to the center of the scratch. The second derivatives of the image are computed along the horizontal, vertical and diagonal directions using directional derivative operators. The magnitude of the four directional derivatives then are compared at each point to generate edge strength and direction images as described below.

An edge strength image is an image in which the intensity of each edge pixel is proportioned to the derivative of the point in a direction which provides the maximum derivative. Brighter edges have larger derivatives whereas weak edges have small derivatives. An edge direction image (not shown) is an image in which the value of each pixel is assigned in accordance with the direction of the edge pixel. The edge strength image (see FIG. 23) is computed by setting each pixel of the edge strength image to the value of the corresponding pixel in one of the four directional derivative images which has the maximum absolute value.

Figure 23:
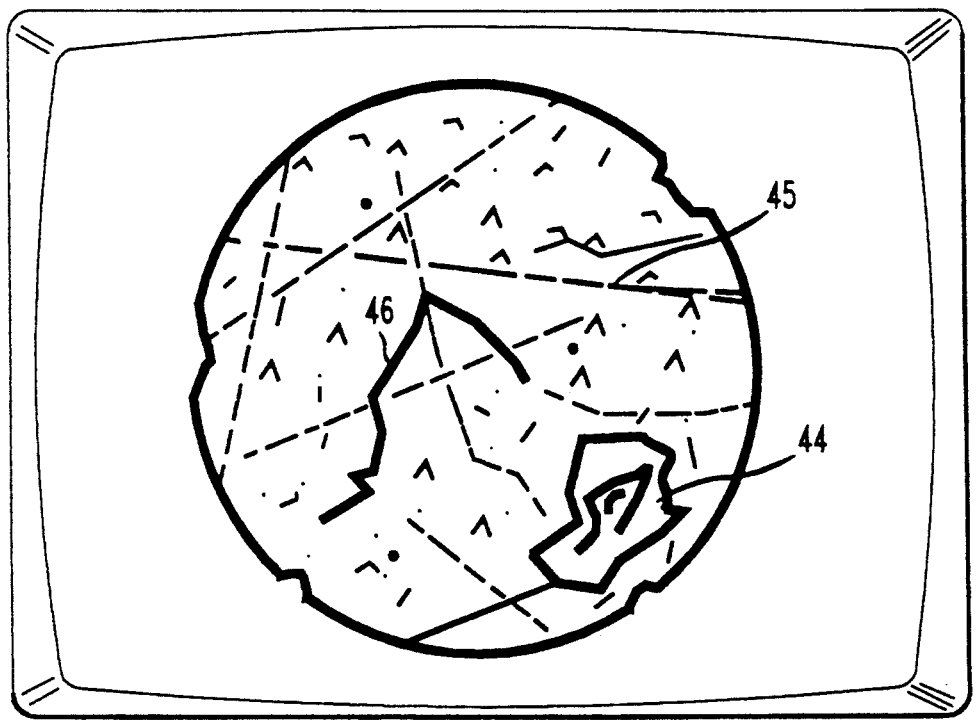
FIG. 23 is a view of an edge strength image prior to thinning.

Because scratches are brighter than the fiber, the strength image computed in this way will have a negative peak at the center and two positive peaks on opposite sides of the scratch. Cracks, on the other hand, are usually darker than the background and sometimes have both a dark and a bright side. However, when using a combined image, cracks behave similar to scratches. The distinction between cracks and scratches still can be made based on the processed difference image. For detection purposes, it is sufficient to retain the pixels with a negative maximum (in absolute value) second derivative. The threshold is set below zero to discard edge pixels arising from extremely weak features or noise and leave pixels with negative derivatives of relatively large magnitude. FIG. 23 shows the edge strength image after thresholding but prior to thinning.

Information about the direction of edge pixels is computed and stored in an edge direction image. A direction image quantized in four directions can be computed simply by recording which of the four directional derivative images is maximum for a given pixel. In order to obtain a more accurate representation, a curve is fitted to the values of the four derivatives and the peak of the fitted curve corresponds to the direction which has the maximum value.

The strength and direction images are used to perform thinning of the edge segments (see FIG. 24) to a width of one pixel.

Edge Tracing and Decomposition

Figure 25:
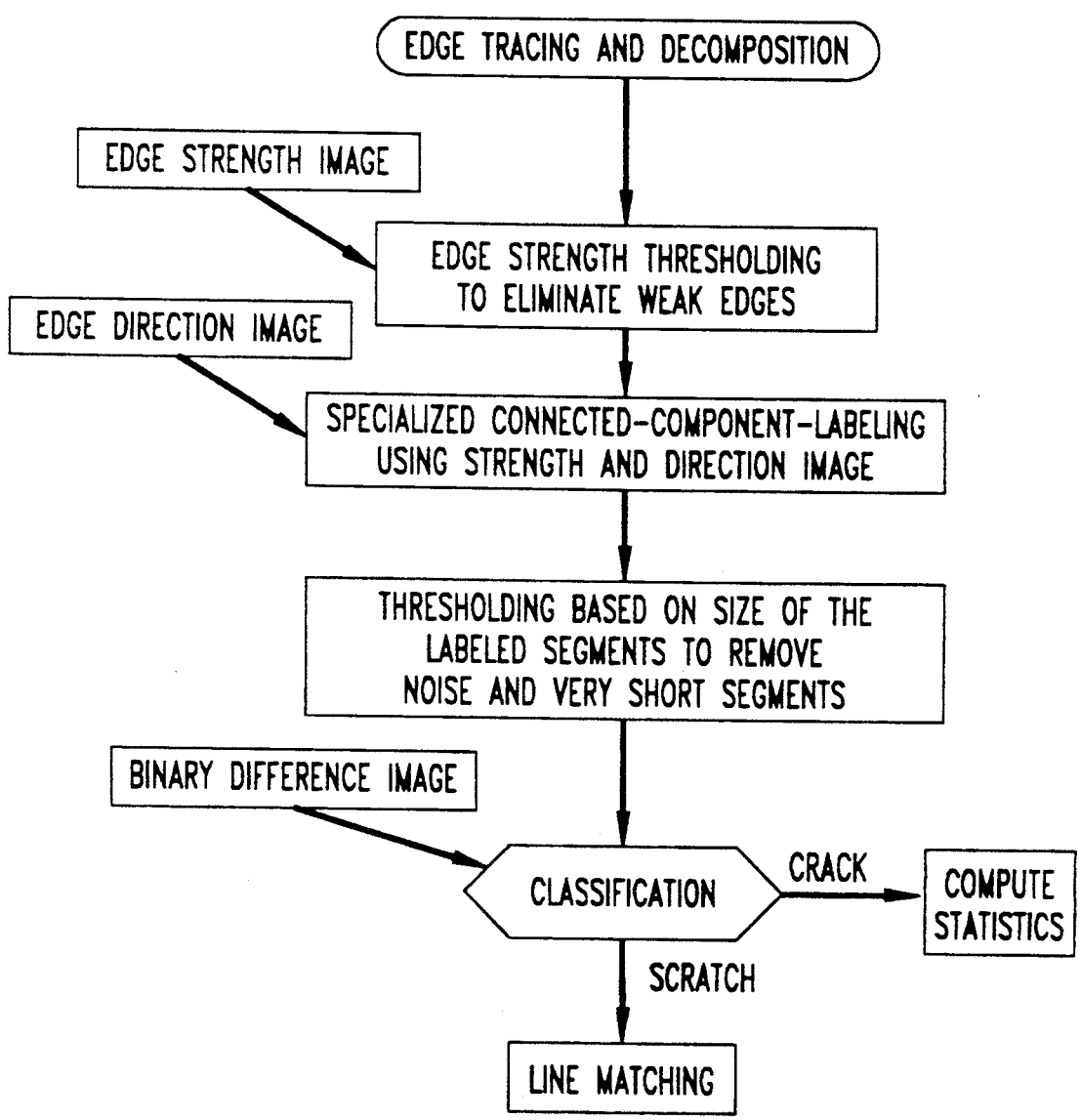
FIG. 25 is a flow chart which depicts a subprocess of the method for edge tracing and decomposition.

The next step in the detection of scratches and cracks is referred to as edge tracing and decomposition and is depicted in the flow chart of FIG. 25. The combined image includes a plurality of segments. The process of the invention is able to make sense of an image having such a plurality of segments and to use acquired information to classify polished ferrules which terminate optical fibers.

A chip or a pit has a sharp boundary. If edge detection were applied to a chip, an edge would be obtained and this could be mistaken as a crack. This problem is overcome by the technique of growing or dilation.

Figure 21:
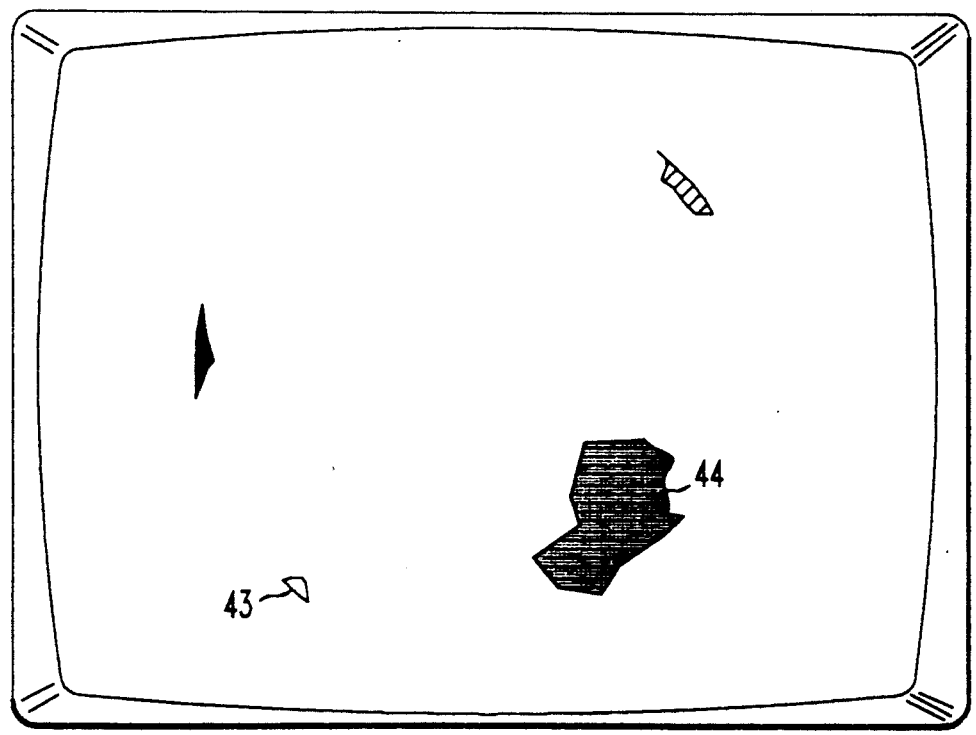
FIG. 21 is an image after opening, component labeling and size thresholding have been performed.
Figure 24:
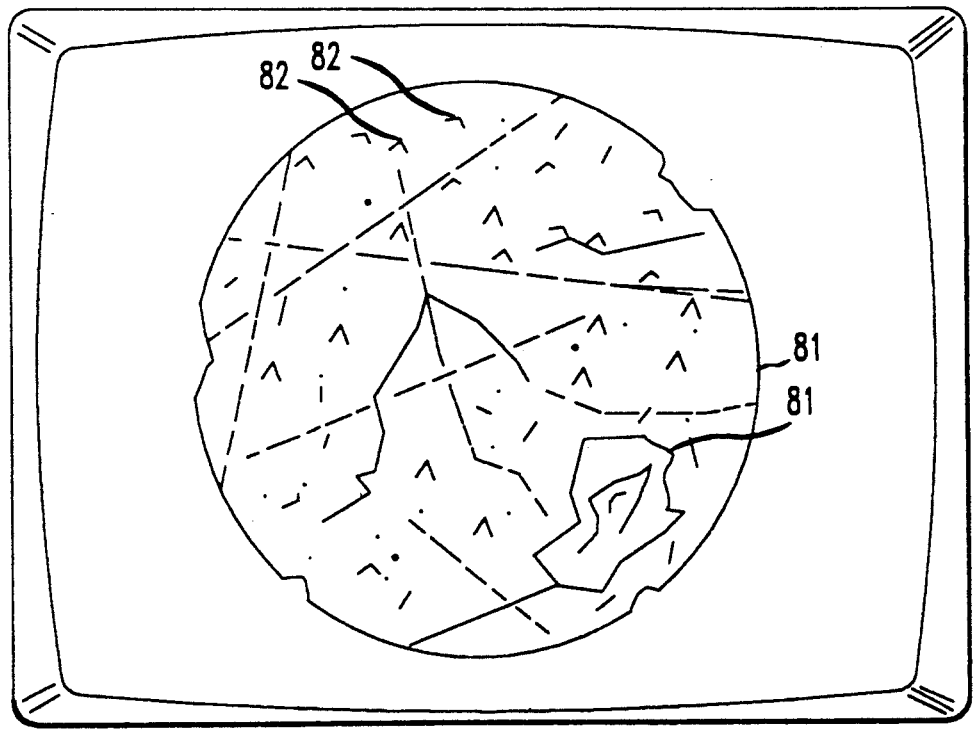
FIG. 24 is a view of the image of FIG. 23 after thinning.

More specifically, FIG. 21 depicts an image in which chips and pits have been found. FIG. 24 is an edge strength image after thinning and as can be seen includes so-called false edges 81—81 which do not represent cracks or scratches. The image of FIG. 21 is grown and superimposed on the image of FIG. 24. This causes the image of FIG. 24 to be zero wherever a chip or pit occurs. The edges which result from the boundary of the fiber also are masked out. What remains is an image which includes noise and strong edges as well as weak edges, but no false edges. Thresholding based on edge strength is applied and as a result, weak edges are discarded. The resulting image may include strong noise indicated in FIG. 24 by the numerals 82—82.

The image at this point must be labeled and each edge or segment classified as a crack or as a scratch segment.

Because of overlap between scratches, cracks, pits and chips, edges can be broken into segments. Segments from different scratches and/or cracks can give rise to composite connected edge segments. Before it can be established that several segments comprise the same feature, it becomes necessary to identify connected segments and to decompose the composite segments into separate components. The presence of composite segments rules out the use of a connected component labeling algorithm because labeling based solely on connectedness will fail to decompose these segments. However, because in most cases the transition from one feature segment to another is not smooth, edge direction information may be used in the labeling process to separate the individual components. Without a direction image, the method simply would group the pixels based on connectedness which could result in crossing lines, such as those designated 83 and 84 in FIG. 26, being grouped as a single feature.

Labelling and decomposition is accomplished through an augmented connected component labeling algorithm. Pixels are grouped based on connectedness, also taking into account edge direction information. The algorithm is such as to allow limited changes in edge direction from one edge element to another. As a result, the algorithm is capable of following curved edges and of breaking these edges at sharp corners. At forks in segments the algorithm follows the path with the least change in direction. After all of the edge segments have been decomposed and labeled based on their strength and direction, small segments caused by noise are discarded by size thresholding. The resulting image is shown in FIG. 26.

At this point and after the masking and decomposition described hereinabove, it is unknown which segments are cracks and which are scratches. Because of the problems which may result from cracks, it becomes important to distinguish them from scratches. Also, steps must be taken to avoid matching segments of features belonging to different classes, e.g., scratches and cracks. To do this, classification of features must be performed prior to line matching.

Classification

Figure 26:
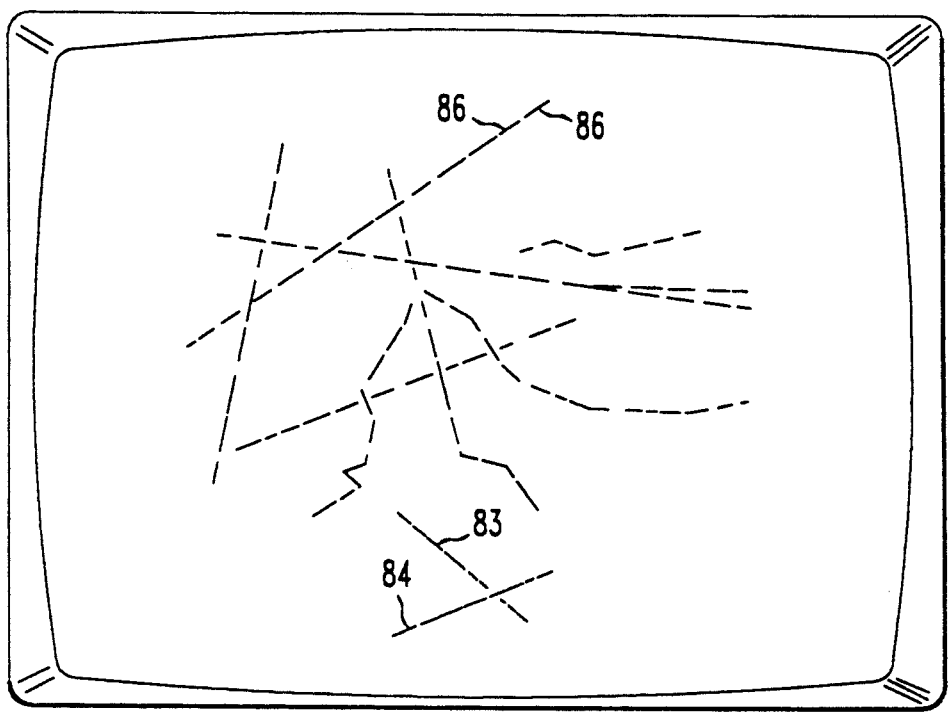
FIG. 26 is a view of an image acquired following artifact edge masking.

Classification is accomplished by using the processed binary difference image and the image which results from thresholding the labeled segments of FIG. 26. That information in the binary difference image which corresponds to that in FIG. 26 is important. The difference image depicts how the image is changed in going from one auxiliary image to the other. If a crack appears in the first and in the second auxiliary image, the crack behaves differently at the two auxiliary focus positions. There are no scratches in the difference iamge, because typically scratches change symmetrically in the auxiliary images and are discarded when the auxiliary images are subtracted. Cracks, on the other hand, do not change symmetrically as a function of focus, becauses they have significant depth.

If it is possible to cover a segment in FIG. 26 with a blob that appears in the binary difference image (see FIG. 10), then it is a crack. More specifically, each segment resulting from the edge tracing and decomposition is classified as a crack if the majority of the corresponding pixels, that is, pixels at the same locations, in the difference image are non-zero. Otherwise, the segment is classified as a scratch (see FIGS. 22 and 25).

Line Matching

Line matching becomes necessary because the line features obtained as a result of applying the edge detection technique to the image and component labeling often are broken into several segments. Segments such as those shown in FIG. 26 and designated by the numerals 86—86 belonging to the same feature need to be grouped together before quantitative information about the feature can be computed. Each line segment is characterized by distance from a center of the image, its direction, and where the line starts and where it stops, etc.

Figure 27:
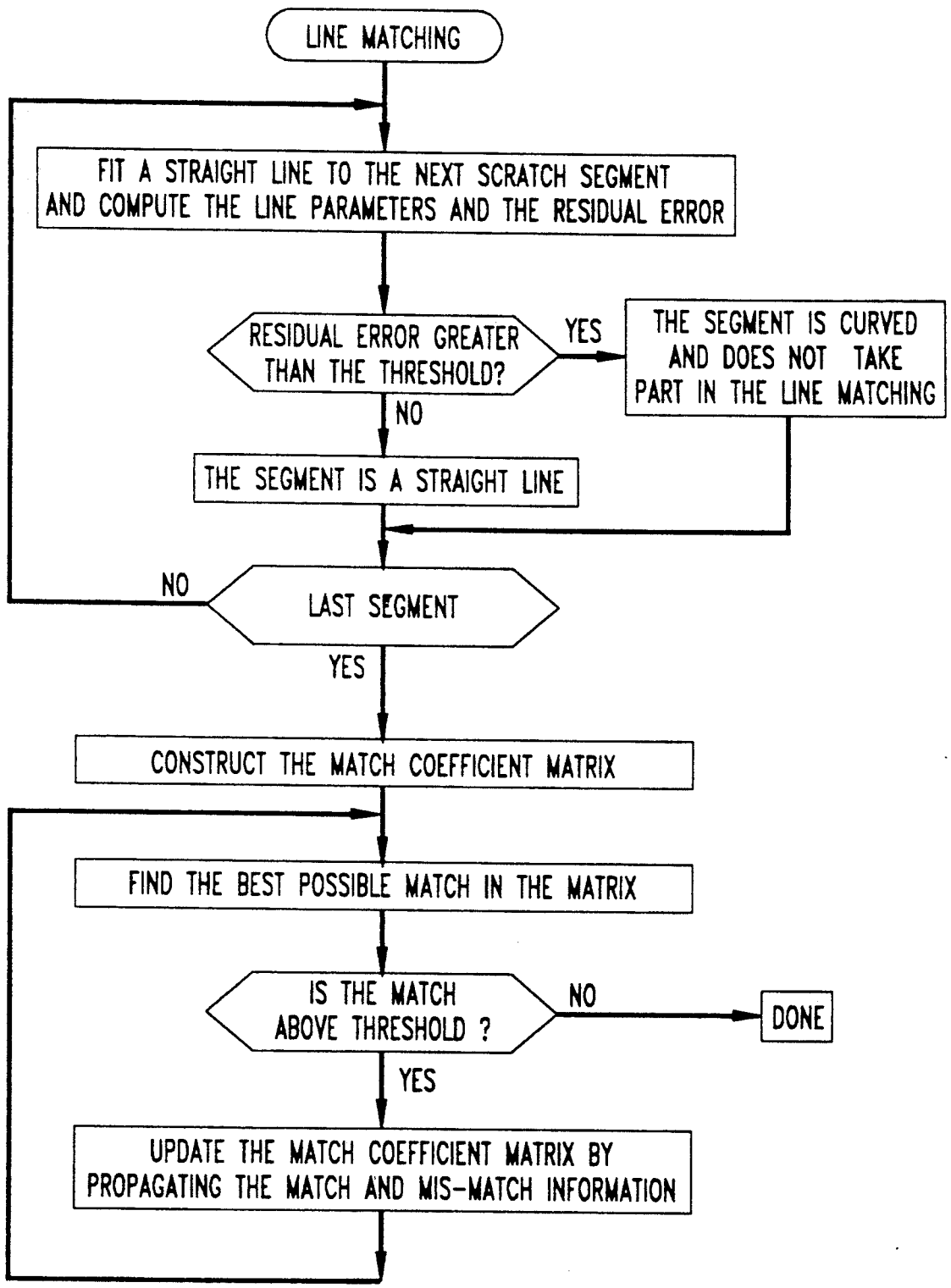
FIG. 27 depicts a flow chart which shows a subprocess for line matching.

The next sequence of steps (see FIG. 27) is used to determine logically which segments are associated with each other and hence need to be matched up. This is done by assigning to each two line segments a match coefficient. The process is to look for two line segments which have a good match coefficient above a given threshold.

The method includes an algorithm for matching straight line segments which are associated with the same line. Briefly, a search is made for two lines which have a sufficiently large match coefficient. The process results in the piecing together two line segments and the providing of a single coefficient representing both segments. Following this, a search is made to determine which other lines, within a predetermined threshold, match.

Because scratches comprise the major portion of edge features present on an end face of a terminated optical fiber and because the majority of these are straight lines, the line matching algorithm is applicable to a large percentage of the scratches. On the other hand, cracks may not be straight. However, the ability of the component labeling method to follow curved lines reduces the number of segments a curved crack is broken into. At this point in the method, no attempt is made to match curved line segments, and if such are present, they will be quantified separately.

In a first step of this subprocess (see FIG. 27) of the method, the components are provided with a higher level of representation which is suitable for matching. A straight line identified by its orthogonal distance, d (see FIG. 28), from the center of the end face of the fiber and the angle, $\theta$, which it makes with the X axis is fitted to each component using least squares approximation. Also, the end points of the fitted line are computed by projecting the end points of the data into the fitted line. The mean of squared differences between the data and the approximating line is used to separate straight segments from curved ones by applying a fixed threshold.

Two potential problems must be avoided. First, the algorithm must be such that closely spaced, parallel line segments are not matched. Also, two short and very distant line segments with no line segments therebetween must not be matched.

Figure 29:
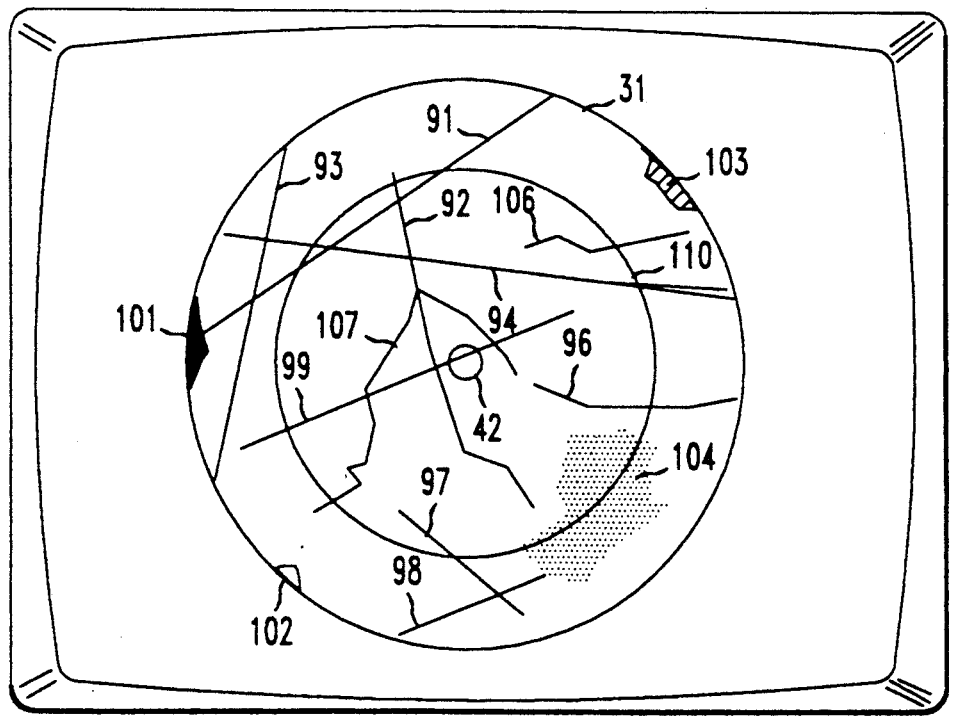
FIG. 29 is a view of a final image from which information about the polished fiber end face is gathered and decisions made therefrom.

The process assigns weights to facilitate matching and arrive at matching coefficients which are arranged in a matrix. The process which is accomplished by matching closely adjacent lines is an iterative one. For two line segments, a parameter referred to as correction factor (CF) is used to modulate the matching coefficient. The correction factor is telltale as to whether two lines are close or far apart. If two line segments are far apart, it is desired that the correction factor be a small number. On the other hand, if there is a small distance separating two line segments, it is desired that CF be a large number. What results from an acceptable match is a new line. Then the process is repeated and the first combination line, resulting from a match up of two segments, may match another line. Through the iterative process, all matchable segments eventually are connected together and FIG. 29 is arrived at to show significant matches. The disjointed segments of the features of FIG. 26 one joined together.

Figure 28:
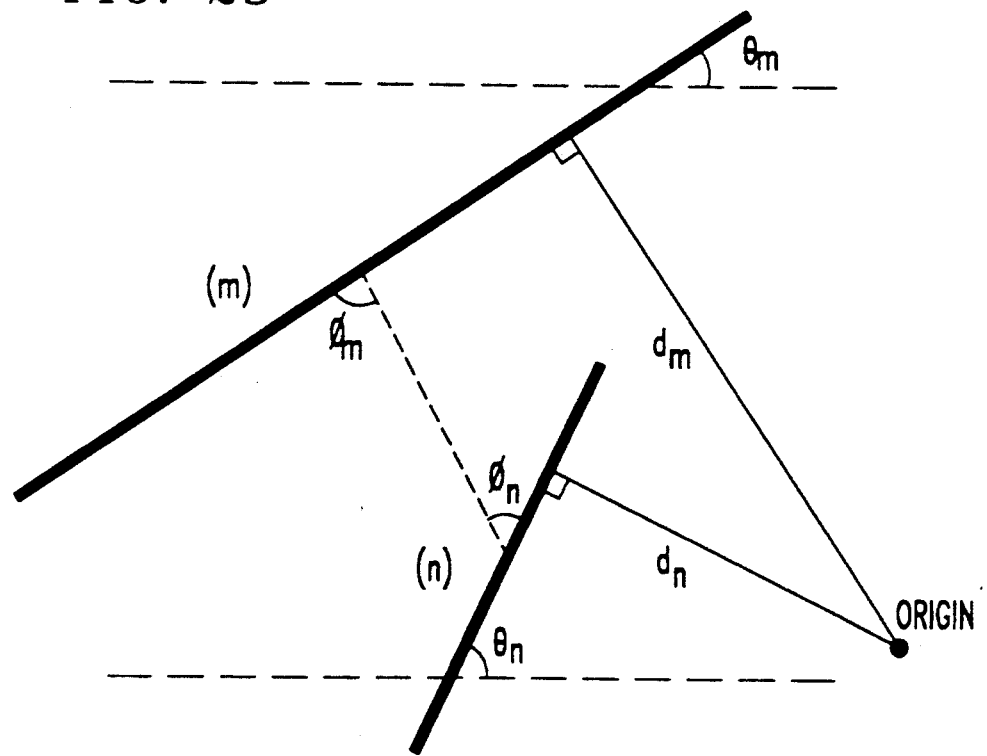
FIG. 28 is a schematic view of two lines with mathematical representations associated therewith.

The matching coefficient is determined as follows. As shown in FIG. 28, $\phi_m$ and $\phi_n$ identify angles that a line which connects the centers of lines m and n makes with lines m and n, respectively. The distance $D_{m,n}$ between lines m and n is defined as $$D_{m,n} = MAX(\phi_m, \phi_n).$$

Then, a match coefficient $M_D(m,n)$ is defined as 0 if any of the following three conditions is true:

$$\delta_d(d_m, d_n) > d_{th} \text{ or}$$

$$\delta_\theta(\theta_m, \theta_n) > \delta_{th} \text{ or}$$

$$D_{m,n} > D_{th}.$$

Otherwise, the match coefficient is defined as $$1 - \frac{D_{m,n}}{D_{th}}.$$

In the foregoing, $\delta_d(d_m, d_n)$ and $\delta_\theta(\theta_m, \theta)$ are the differences between the d and $\theta$ parameters for the two line segments m and n and where $d_{th}$ and $\theta_{th}$ and $D_{th}$ are predetermined thresholds on $\delta_d$, $\delta_\theta$ and $D_{m,n}$, respectively. Each of the above three conditions is checked sequentially. The measure is most sensitive to non-collinear line segments the centers of which are close to each other in which case the line connecting the centers of the two segments makes large angles with the two segments. As the centers of the line segments become further spaced apart, the distance measure decreases which leads to a larger match coefficient. In order to control this property effectively and prevent the matching of lines which are too far from each other, a penalty is imposed on the distance measure using a correction factor CF(m,n) based on the ratio of the length of the line, l, connecting the centers, to the sum of the lengths of the line segments.

$$M(m,n) = M_D(m,n) CF(m,n).$$

The correction factor is defined as $$CF(m,n) = 1 - \alpha \left[ \frac{L(1)}{L(m) + L(n)} \right]$$

where L denotes the length of a line and $\alpha$ is a constant which controls the significance attached to the length ratio.

Advantageously, the line matching method does not depend substantially on the accuracy of the match coefficients in deciding whether or not the line segments are collinear. Instead, it utilizes information about the pairwise match coefficients to find in an iterative manner the best possible matches and to propagate the information about pair-wise mismatches to other line segments.

Assuming N line segments, line matching is accomplished by constructing an N×N match coefficient matrix $$C = \{c_{i,j}, i = 1, \ldots, N, j = 1, \ldots, N\}$$

where the initial values for the match coefficients are given by $$c_{i,j} = c_{j,i} = \begin{cases} 1 & i = j \\ M(i,j) & i \neq j \end{cases}$$

In the first iteration, the match coefficient matrix is searched for the largest (smaller than 1) coefficient $c_{p,q}$ where p and q are line segments. If $c_{p,q}$ is larger than a predetermined match threshold $C_{th}$, lines p and q are marked as matched by setting $$c_{p,q} = c_{q,p} = 1.$$

Subsequently, the pairwise match coefficients of each of two lines with all the other lines are updated by setting the corresponding coefficients equal to the minimum of the two, i.e.

$$c_{p,i} = c_{i,p} = c_{q,i} = c_{i,q} = \begin{cases} 1 & \text{if } c_{p,i} = 1 \text{ or } c_{q,i} = 1 \\ \text{MIN}(c_{p,i}, c_{q,i}) & \text{otherwise} \end{cases}$$

As a result, any mismatch between line p and a third line q is propagated to line q. Additional iterations are carried out by finding the next largest match coefficient (that is, smaller than or equal to $c_{p,q}$) in the updated matrix and repeating the process. A single line extends through two segments and it together with other segments are assigned line match coefficients in an iterative process.

The process of updating match coefficients is complicated by the fact that a match may be made between a single line and a group of already matched lines or two groups of lines. Hence, it is necessary to update the coefficients of all the lines involved by setting them equal to the smallest of the corresponding coefficients in all of them. The iterative process is terminated when the next largest match coefficient is smaller than the predetermined match threshold, $C_{th}$.

By performing the matches in order and propagating information about conflicting matches, the algorithm is able to group segments of straight lines while avoiding incorrect matching between close, but distinct lines. The correction factor CF compensates for the fact that the distance $D_{m,n}$ tends to decrease as the line segments become more distant, and, by overcompensating $M_D(m,n)$ for distances (i.e. larger values of $\alpha$), it can impose an order in the matching process which favors matching closer segments first. More distant lines are matched eventually if they are not in conflict with existing matches.

At the termination of the matching process, each group of matched lines is combined into a single feature and quantitative information about each feature is computed.

In FIG. 29 is depicted the final product image. All trash has been eliminated, chips therein have been identified as have scratches and cracks. The lines surviving size and intensity thresholding are shown in FIG. 29. An example of how decision making can be applied by analyzing the position of defects within the circular areas of FIG. 29 is as follows. Scratches are designated as 91, 92, 93, 94, 96, 97, 98 and 99. Three chips appear in the image and are designated 101, 102, and 103. The numeral 104 designates a pit because its boundaries are inside the fiber boundary. Lines designated 106 and 107 are classified as cracks since their position corresponds to non-zero pixels in the binary difference image of FIG. 10. Rules applied for an acceptable polished surface may include the absence of cracks in an area bounded by a circle 110 and the absence of defects of any kind within the core 42. Should any defects occur in the core or any cracks occur within the area bounded by the circle 110, the polished, terminated optical fiber is declared to be non-acceptable.

It is to be understood that the above-described arrangements are simply illustrative of the invention. Other arrangements may be devised by those skilled in the art which will embody the principles of the invention and fall within the spirit and scope thereof.

We claim:

1. A method of detecting, classifying and quantifying defects in a polished end face of an optical fiber, said method comprising the steps of:
   acquiring images of an end face of a fiber at an optimum focal position and at auxiliary positions behind and in front of said optimum focal position;
   generating a combined image of the fiber end face which depicts any features of interest which exist only in the end face of the optical fiber;
   identifying features of interest which exist only in the end face of the optical fiber; and
   comparing quantitative data generated for each of the features of interest with acceptable values to determine the acceptability of the polished end face of the optical fiber.

2. A method of detecting, classifying and quantifying defects in a polished end face of an optical fiber, which is terminated in a connector component, said method comprising the steps of:
   acquiring images of an end face of a fiber, which has been terminated by a connector component, at an optimum focal position and at auxiliary positions behind and in front of said optimum focal position;
   generating a combined image of the terminated optical fiber end face which depicts any feature of interest which exist only in said terminated end face;

isolating the end face of the optical fiber from the materials of the connector component which terminates the fiber to provide an image which depicts any features of interest which exist only in the end face of the optical fiber;

identifying the features of interest which exist only in the end face of the optical fiber; and comparing quantitative data generated for each of the features of interest with acceptable values to determine the acceptability of the terminated optical fiber.

3. A method of detecting, classifying and quantifying defects a polished end face of a terminated optical fiber, said method comprising:

generating a focus function of the end face of a ferrule in which the optical fiber is terminated;

determining a location of the focus function where the focus of the terminated end face of the fiber is optimum;

acquiring a primary image of the end face of the fiber at the optimum focus location;

acquiring auxiliary images of the end face of the fiber behind and in front of the optimum focus location;

storing the acquired primary and auxiliary images;

providing a difference image which is the absolute value of the difference between the auxiliary images;

thresholding the difference image;

refining the difference image to discard portions of the difference image which result from minor variations between the two auxiliary images;

smoothing the refined difference image to change binary lines in said refined difference image to lines having a generally gradually varying distribution;

comparing pixels between the primary image and smoothed difference image to provide a combined image which depicts any scratches and cracks in the fiber end face;

isolating the fiber portion of the primary image from materials of the ferrule to provide an image which depicts any feature of interest which exists only in the end face of the optical fiber;

detecting and quantifying chips and pits in the isolated combined image;

detecting and determining edge strength and direction of lines in said isolated combined image;

identifying cracks which exist in the end face of the optical fiber and which appear in said isolated combined image;

tracing edges in the isolated combined image and decomposing them into segments;

matching line segments in the isolated combined image; and comparing quantitative data generated for each of the features of interest with acceptable values to determine the acceptability of the terminated optical fiber.

4. The method of claim 3, wherein said method includes the steps of:

acquiring an image of the end face of the terminated optical fiber;

analyzing the high frequency content of each of a plurality of subregions of the image;

verifying a distribution of the focus function and adjusting the focus, if necessary, to establish an optimum, primary focus position;

acquiring an image at a first auxiliary position spaced from said optimum focus position; and acquiring an image at a second auxiliary postition spaced from the first auxiliary position with the primary focus position therebetween.

5. The method of claim 3, wherein said step of providing a combined image includes the step of;

comparing the smoothed difference image with the primary image to provide a combined image each pixel of which is equal to the greater of the corresponding pixels in the smoothed and primary images.

6. The method of claim 3, wherein said step of isolating the fiber includes the steps of:

thresholding the combined image;

morphologically opening the thresholded primary image to separate a ring of adhesive material, which is disposed between said optical fiber and its terminating ferrule to hold the fiber in the ferrule, into discrete areas;

filtering the discrete areas of adhesive material and discarding the discrete areas which are less than a predetermined size;

estimating the center of the end face of the optical fiber;

determining the radius of the end face of the optical fiber; and defining a circular mask to isolate the end face of the optical fiber.

7. The method of claim 3, wherein said step of detecting chips and pits includes the steps of:

thresholding the portion of the combined image which falls within the isolated optical fiber end face to provide an image which contains chips and pits;

morphologically closing the image to merge adjacent ones of the chips and pits;

morphologically opening the morphologically closed image to remove noise and relatively small components;

identifying individual chips and pits; and quantifying the chips and pits which appear in the end face of the optical fiber.

8. The method of claim 3, wherein said step of detecting and determining edge strength and direction of lines includes the steps of:

stretching the intensity of the isolated portion of the combined image to provide an image in which features appearing in the fiber end face are enhanced;

smoothing the enhanced image to reduce noise and to shape the intensity profile of edges in the enhanced image;

computing derivatives in horizontal, vertical and diagonal directions;

determining the strength and direction of edges in the smoothed enhanced image to provide edge strength and direction images; and thinning edges to have a width of a single pixel.

9. The method of claim 8, which also includes tracing and decomposing of edges which includes the steps of:

thresholding the edge strength image to discard edges having a strength less than a predetermined value;

labeling connected components from said edge strength image;

thresholding the labeled component image to remove noise and relatively short segments; and identifying cracks from the thresholded images by determining the correspondence with non-zero pixels in the binary difference image.

10. The method of claim 9, wherein said lines which appear in said thresholded, labeled component image and which are not cracks are processed to match line segments and to identify scratches.

11. The method of claim 10, wherein the step of line matching includes the step of providing a matrix which for the pairing of each two lines which appear in said thresholded image, a matching coefficient is provided.

12. The method of claim 11, wherein a corrected matching coefficient which is equal to the product at the matching coefficient and a correction factor, which provides an indication of the separation between line segments, is used in matching line segments.

13. The method of claim 12, wherein said step of line matching comprises an iterative process.

14. The method of claim 13, wherein a final image includes chips, pits, scratches and cracks of interest which are identified.

15. The method of claim 14, wherein any defects which appear in the final image are quantified and the quantification compared to predetermined values to decide whether or not the polished end face of the terminated optical fiber is acceptable.

* * * * *